United States Patent [19]
Holton et al.

[11] Patent Number: 6,066,747
[45] Date of Patent: May 23, 2000

[54] PROCESS FOR THE PREPARATION OF 9-DESOXOTAXANES

[75] Inventors: Robert A. Holton, Tallahassee, Fla.; Carmon Somoza, Corvallis, Oreg.; Yukio Suzuki, Sendai; Mitsuru Shindo, Tokyo, both of Japan

[73] Assignee: Florida State University, Tallahassee, Fla.

[21] Appl. No.: 08/522,307

[22] PCT Filed: Mar. 4, 1994

[86] PCT No.: PCT/US94/02382

§ 371 Date: Oct. 30, 1995

§ 102(e) Date: Oct. 30, 1995

[87] PCT Pub. No.: WO94/20485

PCT Pub. Date: Sep. 15, 1994

[51] Int. Cl.[7] .................................................. C07D 305/14
[52] U.S. Cl. .......................................... 549/510; 549/511
[58] Field of Search ..................................... 549/510, 511

[56] References Cited

U.S. PATENT DOCUMENTS

| | | | |
|---|---|---|---|
| 4,814,470 | 3/1989 | Colin et al. | 514/449 |
| 4,857,653 | 8/1989 | Colin et al. | 549/511 |
| 4,876,399 | 10/1989 | Holton et al. | 568/817 |
| 4,921,974 | 5/1990 | Duggan | 549/214 |
| 4,924,011 | 5/1990 | Denis et al. | 549/510 |
| 4,924,012 | 5/1990 | Colin et al. | 549/510 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,059,699 | 10/1991 | Kingston et al. | 549/511 |
| 5,136,060 | 8/1992 | Holton | 549/510 |
| 5,175,315 | 12/1992 | Holton | 549/510 |
| 5,227,400 | 7/1993 | Holton et al. | 514/444 |
| 5,229,526 | 7/1993 | Holton | 549/213 |
| 5,243,045 | 9/1993 | Holton et al. | 544/60 |
| 5,250,683 | 10/1993 | Holton et al. | 544/60 |
| 5,254,703 | 10/1993 | Holton | 549/510 |
| 5,264,591 | 11/1993 | Bombardelli et al. | 549/214 |
| 5,274,124 | 12/1993 | Holton | 549/214 |
| 5,283,253 | 2/1994 | Holton et al. | 514/444 |
| 5,284,864 | 2/1994 | Holton et al. | 514/449 |
| 5,284,865 | 2/1994 | Holton et al. | 549/510 |
| 5,336,785 | 8/1994 | Holton | 549/214 |
| 5,338,872 | 8/1994 | Holton et al. | 549/510 |
| 5,350,866 | 9/1994 | Holton et al. | 549/510 |
| 5,352,806 | 10/1994 | Gunawardana | 549/510 |
| 5,384,399 | 1/1995 | Holton | 544/97 |
| 5,399,726 | 3/1995 | Holton et al. | 549/510 |
| 5,405,972 | 4/1995 | Holton et al. | 549/214 |
| 5,430,160 | 7/1995 | Holton | 549/510 |
| 5,440,056 | 8/1995 | Klein et al. | 549/510 |
| 5,466,834 | 11/1995 | Holton | 549/510 |
| 5,489,601 | 2/1996 | Holton et al. | 514/337 |
| 5,532,363 | 7/1996 | Holton | 544/97 |
| 5,539,103 | 7/1996 | Holton | 540/354 |

FOREIGN PATENT DOCUMENTS

| | | |
|---|---|---|
| 0 253 738 | 1/1988 | European Pat. Off. . |
| 0 253 739 | 1/1988 | European Pat. Off. . |
| 0 336 840 | 10/1989 | European Pat. Off. . |
| 0 336 841 | 10/1989 | European Pat. Off. . |
| 0 247 378 | 9/1990 | European Pat. Off. . |
| 0 400 971 | 12/1990 | European Pat. Off. . |
| 0 428 376 | 5/1991 | European Pat. Off. . |
| 0 534 707 | 3/1993 | European Pat. Off. . |
| 0 534 708 | 3/1993 | European Pat. Off. . |
| 0 534 709 | 3/1993 | European Pat. Off. . |
| 91/9224 | 11/1991 | South Africa . |
| 92/09589 | 6/1992 | WIPO . |
| 93/02065 | 2/1993 | WIPO . |
| 94/08984 | 4/1994 | WIPO . |

OTHER PUBLICATIONS

Klein, L, Tetrahedron Letters, vol. 34, No. 13, pp. 2047–2050, 1993.

L. Zamir et al. "Taxanes Isolated from *Taxus Canadensis*" Tetrahedron Letters, vol. 33, No. 36, pp. 5173–5176 (1992).

Gunawardana et al. "Isolation of 9–Dihydro–13–Acetylbaccatin III from *Taxus Canadensis*" Journal of National Products, vol. 55, No. 11, pp. 1686–1689, Nov. 1992.

Bartholomew et al., "A Novel Rearrangement Reaction Conversion of 3–(chloromethyl)azetidin–2–ones to Azetidine–3–carboxylic Acid Esters", Tetrahedron Letters, vol. 32, No. 36 (1991) pp. 4795–4798.

Borman, "New Family of Taxol, Taxotere Analogs Developed" Science & Technology, Chemical & Engineering News, Apr. 12, 1993.

Chen et al., "Taxol Structure–Activity Relationships: Synthesis and Biological Evaluation of 2–Deoxytaxol" Tetrahedron Letters, vol. 34, No. 20 (1993) pp. 3205–3206.

Denis et al. "A Highly Efficient, Practical Approach to Natural Taxol", Journal of American Chemical Soc., vol. 110, (1988) pp. 5917–5919.

Deutsch et al. "Synthesis of Congeners and Prodrugs. 3. Water–Soluble Prodrugs of Taxol With Potent Antitumour Activity", Journal of Medicinal Chem., vol. 32, No. 4 (Apr. 1989) pp. 788–792.

Farina et al. "The Chemistry of Taxanes: Unexpected Rearrangement of Baccatin III During Chemoselective Debenzoylation With $Bu_3SnOMe/LiCl$", Tetrahedron Letters, vol. 33, No. 28 (1992) pp. 3979–3982.

Holton "Synthesis of the Taxane Ring System" Journal of American Chemical Soc., vol. 106 (1984) pp. 5731–5732.

Holton et al., "A Synthesis of Taxusin", Journal of American Chemical Soc., vol. 110 (1988) pp. 6558–6560.

Kaiser et al. "Synthesis of Esters of Acid–Unstable Alcohols by Means of n–butyllithium" Journal of Organic Chemistry, vol. 35 (1970) p. 1198.

Kingston et al. "Progress in the Chemistry of Organic Natural Products" Springer–Verlag, New York (1993) pp. 1–206.

(List continued on next page.)

*Primary Examiner*—Ba K. Trinh
*Attorney, Agent, or Firm*—Senniger, Powers, Leavitt & Roedel

[57] ABSTRACT

A derivative or analog of baccatin III or 10-desacetyl baccatin III having a C-9 substituent other than keto.

31 Claims, No Drawings

OTHER PUBLICATIONS

Klein "Synthesis of 9–Dihydrotaxol: A Novel Bioactive Taxane" Tetrahedron Letters, vol. 34, No. 13 (1993) pp. 2047–2050.

Magri et al. "Modified Taxols, 4. Synthesis and Biological Activity of Taxols Modified in the Side Chain" Journal of Natural Products, vol. 51, No. 2 (1988) pp. 298–306.

Miller et al. "Antileukemic Alkaloids From *Taxus Wallichiana* Zucc." Jour. of Organic Chem., vol. 46 (1981) pp. 1469–1474.

Mukerjee et al. "β–Lactams: Retrospect and Prospect" Tetrahedron Letters, vol. 34, No. 52 (1978) pp. 1731–1767.

Ojima et al. "New and Efficient Approaches to the Semisynthesis of Taxol and its C–13 Side Chain Analogs by Means of β–Lactam Synthon Method" Tetrahedron Letters, vol. 48, No. 34 (1992) pp. 6985–7012.

Samaranayake et al. "Modified Taxols. 5.1 Reaction of Taxol with Electrophilic Reagents and Preparation of a Rearranged Taxol Derivative with Tubulin Assembly Activity3." Journal of Organic Chemistry, vol. 56, No. 17 (1991) pp. 5114–5119.

Schultz et al "Synthesis of New N–radicals of Tetrazan–1–yl" Chemical Abstracts, vol. 108, No. 37298C (1988) p. 581.

Senilh et al. "Hemisynthese de noveaux analogues du taxol. Etude de leur interaction avec la tubuline", C.R. Acad. Sc. Paris, Serie II, vol. 229, No. 15 (Nov. 21, 1984) pp. 1039–1043.

Wani et al., "Plant Antitumor Agents. VI. The Isolation and Structure of Taxol, a Novel Antileukemic and Antitumor Agent From *Taxus Brevifolia*" Jurnal of American Chemical Soc., vol. 93, No. 9 (May 5, 1971) pp. 2325–2327.

Witherup et al., "High Performance Liquid Chromatographic Separation of Taxol and Related Compounds From *Taxus Brevifolia*" Journal of Liquid Chromatography, vol. 12, No. 11 (1989) pp. 2117–2132.

International Search Report issued for PCT/US92/07990 dated Dec. 2, 1992.

PROCESS FOR THE PREPARATION OF 9-DESOXOTAXANES

This invention was made with Government support under NIH Grant #CA 42031 and NIH Grant #CA 55131 awarded by the National Institutes of Health. The Government has certain rights in the invention.

This is a 371 of PCT/US94/02382, dated Mar. 4, 1994.

BACKGROUND OF THE INVENTION

The present invention relates to a process for the preparation of taxol, baccatin III and 10-desacetyl-baccatin III derivatives or other taxanes having new C9 functional groups.

Taxol is a natural product extracted from the bark of yew trees. It has been shown to have excellent antitumor activity in in vivo animal models, and recent studies have elucidated its unique mode of action, which involves abnormal polymerization of tubulin and disruption of mitosis. It is currently undergoing clinical trials against ovarian, breast and other types of cancer in the United States and France and preliminary results have confirmed it as a most promising chemotherapeutic agent. The structure of taxol and the numbering system conventionally used is shown below; this numbering system is also applicable to compounds used in the process of the present invention.

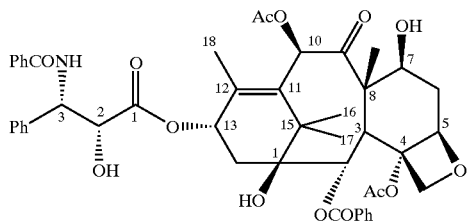

In Colin U.S. Pat. No. 4,814,470, it was reported that a taxol derivative, commonly referred to as taxotere, has an activity significantly greater than taxol. Taxotere has the following structure:

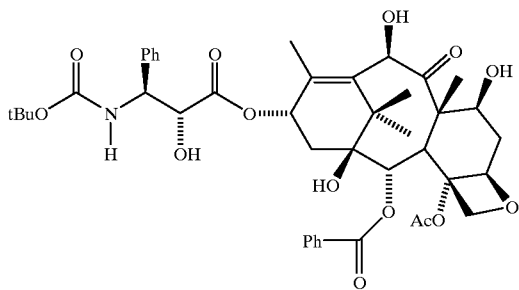

The tetracyclic core of taxol and taxotere bear a C9 keto substituent which, if modified, would lead to the preparation of a series of taxol analogs having improved water solubility. To date, however, the selective manipulation of the C9 keto group has presented a formidable problem.

SUMMARY OF THE INVENTION

Among the objects of the present invention, therefore, is the provision of a process for selectively manipulating the C9 keto substituent of baccatin III, 10-deactylbaccatin III and other taxanes; and the provision of such a process which is relatively straightforward.

Briefly, therefore, the present invention is directed to a process for the preparation of analogs or derivatives of taxol, baccatin III, 10-desacetyl baccatin III or other taxanes in which the C9 keto substituent is reduced to the corresponding hydroxy group. Optionally, the C9 hydroxy substituent may thereafter be selectively replaced by another functional group and/or other substituents of the taxane may be replaced by other functional groups to yield a taxane having the formula:

(1)

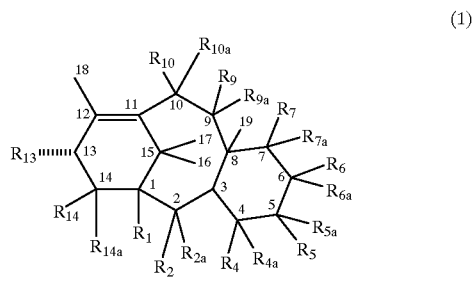

wherein $R_1$ is hydrogen, hydroxy, protected hydroxy or together with $R_{14}$ forms a carbonate;

$R_2$ is hydrogen, hydroxy, —$OCOR_{31}$, or together with $R_{2a}$ forms an oxo;

$R_{2a}$ is hydrogen or together with $R_2$ forms an oxo;

$R_4$ is hydrogen, together with $R_{4a}$ forms an oxo, oxirane or methylene, or together with $R_{5a}$ and the carbon atoms to which they are attached form an oxetane ring;

$R_{4a}$ is hydrogen, alkyl, alkenyl, alkynyl, aryl, heteroaryl, cyano, hydroxy, —$OCOR_{30}$, or together with $R_4$ forms an oxo, oxirane or methylene;

$R_5$ is hydrogen or together with $R_{5a}$ forms an oxo;

$R_{5a}$ is hydrogen, hydroxy, protected hydroxy, acyloxy, together with $R_5$ forms an oxo, or together with $R_4$ and the carbon atoms to which they are attached form an oxetane ring;

$R_6$ is hydrogen, alkyl, alkenyl, alkynyl, aryl, or heteroaryl, hydroxy, protected hydroxy or together with $R_{6a}$ forms an oxo;

$R_{6a}$ is hydrogen, alkyl, alkenyl, alkynyl, aryl, or heteroaryl, hydroxy, protected hydroxy or together with $R_6$ forms an oxo;

$R_7$ is hydrogen or together with $R_{7a}$ forms an oxo;

$R_{7a}$ is hydrogen, halogen, protected hydroxy, —$OR_{28}$, or together with $R_7$ forms an oxo;

$R_9$ is hydrogen;

$R_{9a}$ is hydrogen, hydroxy, protected hydroxy, or acyloxy;

$R_{10}$ is hydrogen or together with $R_{10a}$, forms an oxo;

$R_{10a}$ is hydrogen, —$OCOR_{29}$, hydroxy or protected hydroxy, or together with $R_{10}$ forms an oxo;

$R_{13}$ is hydroxy, protected hydroxy or

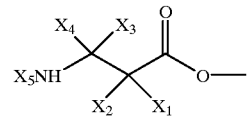

$R_{14}$ is hydrogen, alkyl, alkenyl, alkynyl, aryl, or heteroaryl, hydroxy, protected hydroxy or together with $R_1$ forms a carbonate;

$R_{14a}$ is hydrogen, alkyl, alkenyl, alkynyl, aryl, or heteroaryl;

$R_{28}$ is hydrogen, acyl, or hydroxy protecting group;

$R_{29}$, $R_{30}$ and $R_{31}$, are independently hydrogen, alkyl, alkenyl, alkynyl, monocyclic aryl or monocyclic heteroaryl;

$X_1$ is $-OX_6$, $-SX_7$, or $-NX_8X_9$;

$X_2$ is hydrogen, alkyl, alkenyl, alkynyl, aryl, or heteroaryl;

$X_3$ and $X_4$ are independently hydrogen, alkyl, alkenyl, alkynyl, aryl, or heteroaryl;

$X_5$ is $-COX_{10}$, $-COOX_{10}$, $-COSX_{10}$, $-CONX_8X_{10}$, or $-SO_2X_{11}$;

$X_6$ is hydrogen, alkyl, alkenyl, alkynyl, aryl, heteroaryl, or hydroxy protecting group;

$X_7$ is alkyl, alkenyl, alkynyl, aryl, heteroaryl, or sulfhydryl protecting group;

$X_8$ is hydrogen, alkyl, alkenyl, alkynyl, aryl, heteroaryl, or heterosubstituted alkyl, alkenyl, alkynyl, aryl or heteroaryl;

$X_9$ is an amino protecting group;

$X_{10}$ is alkyl, alkenyl, alkynyl, aryl, heteroaryl, or heterosubstituted alkyl, alkenyl alkynyl, aryl or heteroaryl;

$X_{11}$ is alkyl, alkenyl, alkynyl, aryl, heteroaryl, $-OX_{10}$, or $-NX_8X_{14}$; and $X_{14}$ is hydrogen, alkyl, alkenyl, alkynyl, aryl, or heteroaryl.

The present invention is additionally directed to a derivative of baccatin III or 10-desacetyl baccatin III having the following formula which is a key intermediate in the synthesis of a new series of tetracyclic taxanes

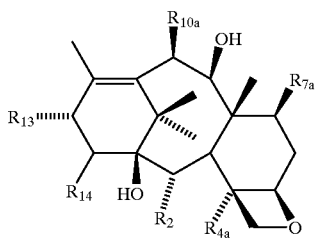

wherein $R_2$, $R_{4a}$, $R_{7a}$, $R_{10a}$ and $R_{14}$ are as previously defined and $R_{13}$ is hydroxy or protected hydroxy.

Other objects and features of this invention will be in part apparent and in part pointed out hereinafter.

DETAILED DESCRIPTION OF THE INVENTION

As used herein "Ar" means aryl; "Ph" means phenyl; "Ac" means acetyl; "Et" means ethyl; "R" means alkyl unless otherwise defined; "tBu" means t-butyl; "TES" means triethylsilyl; "TMS" means trimethylsilyl; "TPAP" means tetrapropylammonium perruthenate; "DMAP" means p-dimethylamino pyridine; "DMF" means dimethylformamide; "LDA" means lithium diisopropylamide; "LAH" means lithium aluminum hydride; "Red-Al" means sodium bis(2-methoxyethoxy)aluminum hydride; "10-DAB" means 10-desacetylbaccatin III; protected hydroxy means $-OR$ wherein R is a hydroxy protecting group; sulfhydryl protecting group" includes, but is not limited to, hemithioacetals such as 1-ethoxyethyl and methoxymethyl, thioesters, or thiocarbonates; "amine protecting group" includes, but is not limited to, carbamates, for example, 2,2,2-trichloroethylcarbamate or tertbutylcarbamate; and "hydroxy protecting group" includes, but is not limited to, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-trichloroethyl; alkenyl carbonates having from two to six carbon atoms such as vinyl and allyl; cycloalkyl carbonates have from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro. Other hydroxyl, sulfhydryl and amine protecting groups may be found in "Protective Groups in Organic Synthesis" by T. W. Greene, John Wiley and Sons, 1981.

The alkyl groups described herein, either alone or with the various substituents defined hereinabove are preferably lower alkyl containing from one to six carbon atoms in the principal chain and up to 15 carbon atoms. They may be straight or branched chain and include methyl, ethyl, propyl, isopropyl, butyl, isobutyl, tert-butyl, aryl, hexyl, and the like.

The alkenyl groups described herein, either alone or with the various substituents defined hereinabove are preferably lower alkenyl containing from two to six carbon atoms in the principal chain and up to 15 carbon atoms. They may be straight or branched chain and include ethenyl, propenyl, isopropenyl, butenyl, isobutenyl, aryl, hexenyl, and the like.

The alkynyl groups described herein, either alone or with the various substituents defined hereinabove are preferably lower alkynyl containing from two to six carbon atoms in the principal chain and up to 15 carbon atoms. They may be straight or branched chain and include ethynyl, propynyl, butynyl, isobutynyl, aryl, hexynyl, and the like.

The aryl moieties described herein, either alone or with various substituents, contain from 6 to 15 carbon atoms and include phenyl. Substituents include alkanoxy, protected hydroxy, halogen, alkyl, aryl, alkenyl, acyl, acyloxy, nitro, amino, amido, etc. Phenyl is the more preferred aryl.

The heteroaryl moieties described herein, either alone or with various substituents, contain from 5 to 15 atoms and include, furyl, thienyl, pyridyl and the like. Substituents include alkanoxy, protected hydroxy, halogen, alkyl, aryl, alkenyl, acyl, acyloxy, nitro, amino, amido, etc.

The acyloxy groups described herein contain alkyl, alkenyl, alkynyl, aryl or heteroaryl groups.

The substituents of the substituted alkyl, alkenyl, alkynyl, aryl, and heteroaryl groups and moieties described herein, may be alkyl, alkenyl, alkynyl, aryl, heteroaryl and/or may contain nitrogen, oxygen, sulfur, halogens and include, for example, lower alkoxy such as methoxy, ethoxy, butoxy, halogen such as chloro or fluoro, nitro, amino, and keto.

In accordance with the present invention, it has been discovered that the C9 keto substituent of a taxane having a C9 keto and a C7 hydroxy substuent may be selectively reduced to yield the corresponding C9 β-hydroxy derivative.

The reducing agent is preferably a an aluminum hydride or a borohydride such as triacetoxyborohydride, more preferably a tetraalkylborohydride or tetraalkylaluminumhydride, and most preferably, tetrabutylammoniumborohydride ($Bu_4NBH_4$).

As illustrated in Reaction Scheme 1, the reaction of baccatin III with $Bu_4NBH_4$ in methylene chloride yields 9-desoxo-9β-hydroxybaccatin III 5. After the C7 hydroxy group is protected with, for example, the triethylsilyl protecting group, a suitable side chain may be attached to 7-protected-9β-hydroxy derivative 6 as set forth in U.S. Pat. Nos. 4,924,011 and 4,924,012 or by reaction with a β-lactam as set forth in U.S. Pat. No. 5,175,315 or copending U.S. patent application Ser. No. 07/949,107. Removal of the remaining protecting groups thus yields 9β-hydroxy-desoxo taxol or other 9β-hydroxytetracylic taxane having a C13 side chain.

Alternatively, the C13 hydroxy group of 7-protected-9β-hydroxy derivative 6 may be protected with trimethylsilyl or other protecting group which can be selectively removed relative to the C7 hydroxy protecting group as illustrated in Reaction Scheme 2, to enable further selective manipulation of the various substituents of the taxane. For example, reaction of 7,13-protected-9β-hydroxy derivative 7 with KH causes the acetate group to migrate from C10 to C9 and the hydroxy group to migrate from C9 to C10, thereby yielding 10-desacetyl derivative 8. Protection of the C10 hydroxy group of 10-desacetyl derivative 8 with triethylsilyl yields derivative 9. Selective removal of the C13 hydroxy protecting group from derivative 9 yields derivative 10 to which a suitable side chain may be attached as described above.

REACTION SCHEME 1

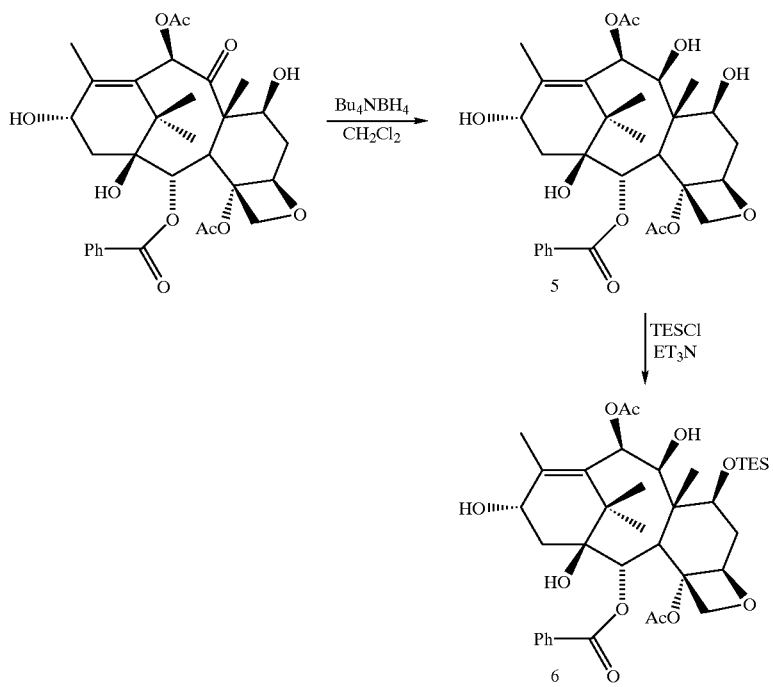

REACTION SCHEME 2

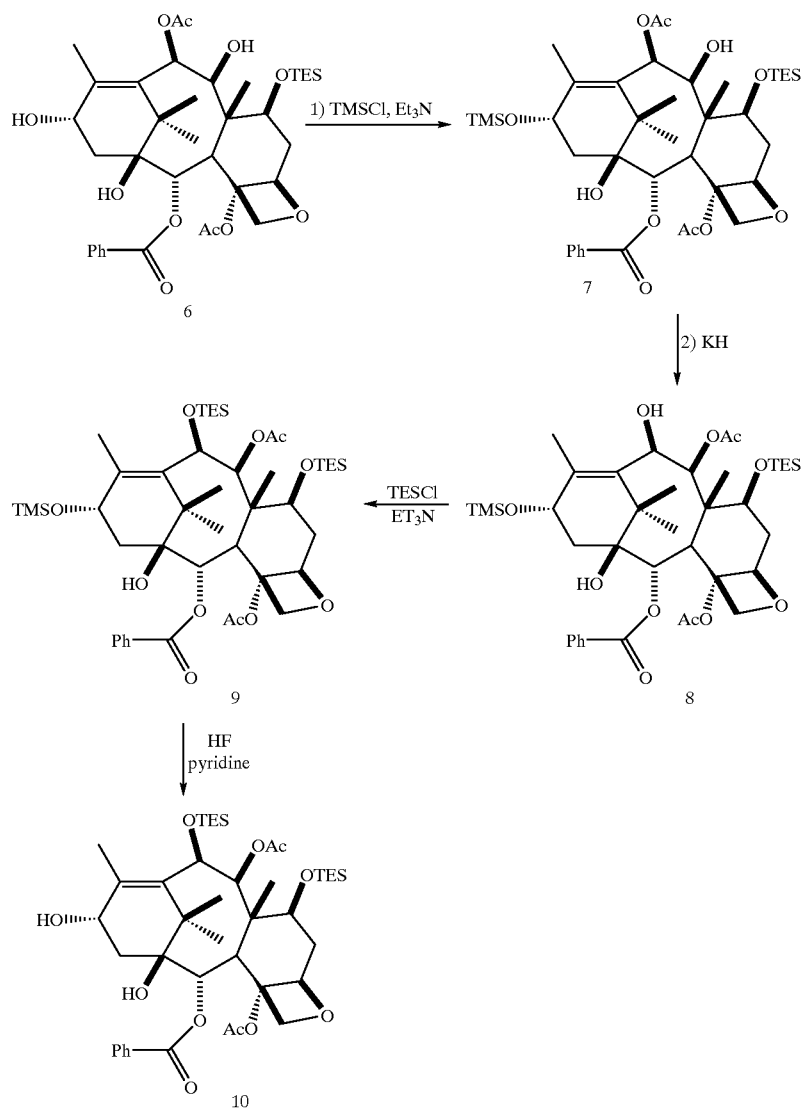

As shown in Reaction Scheme 3, 10-oxo derivative 11 can be provided by oxidation of 10-desacetyl derivative 8. Thereafter, the C13 hydroxy protecting group can be selectively removed followed by attachment of a side chain as described above to yield 9-acetoxy-10-oxo-taxol or other 9-acetoxy-10-oxotetracylic taxanes having a C13 side chain. Alternatively, the C9 acetate group can be selectively removed by reduction of 10-oxo derivative 11 with a reducing agent such as samarium diiodide to yield 9-desoxo-10-oxo derivative 12 from which the C13 hydroxy protecting group can be selectively removed followed by attachment of a side chain as described above to yield 9-desoxo-10-oxo-taxol or other 9-desoxo-10-oxotetracylic taxanes having a 13 side chain.

REACTION SCHEME 3

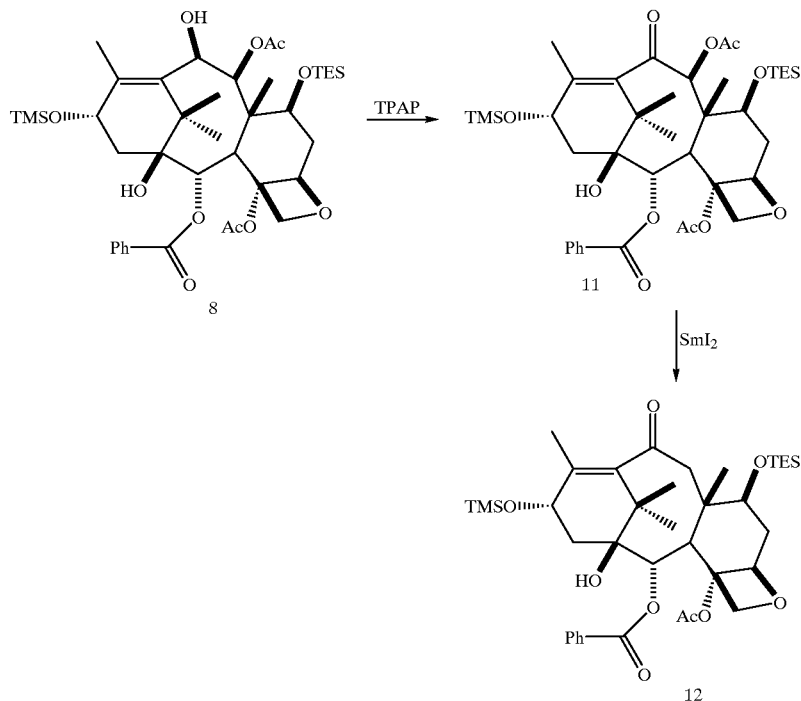

Reaction Scheme 4 illustrates a reaction in which 10-DAB is reduced to yield pentaol 13. The C7 and C10 hydroxyl groups of pentaol 13 can then be selectively protected with the triethylsilyl or another protecting group to produce triol 14 to which a C13 side chain can be attached as described above or, alternatively, after further modification of the tetracylic substituents.

REACTION SCHEME 4

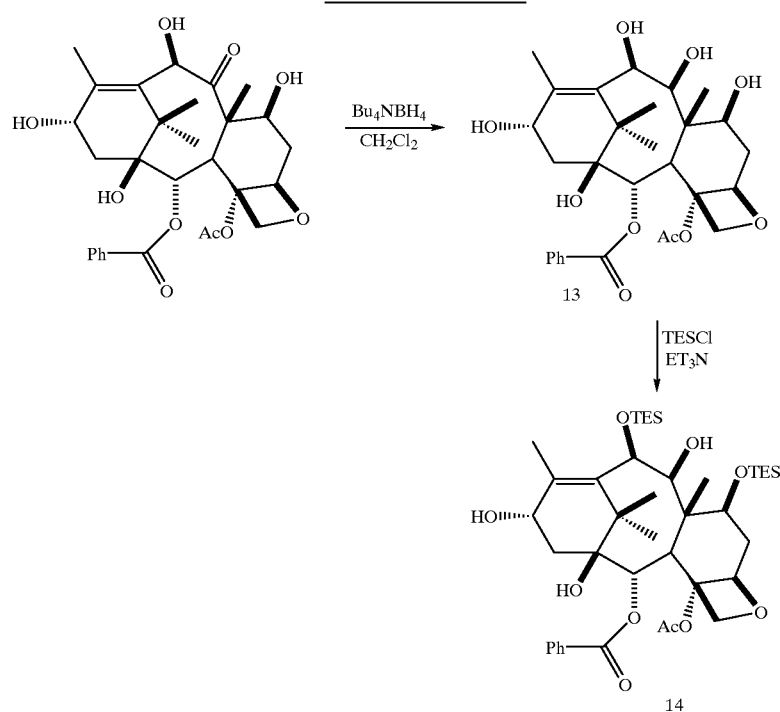

Taxanes having C9 and/or C10 acyloxy substituents other than acetate can be prepared using 10-DAB as a starting material as illustrated in Reaction Scheme 5. Reaction of 10-DAB with triethylsilyl chloride in pyridine yields 7-protected 10-DAB 15. The C10 hydroxy substituent of 7-protected 10-DAB 15 may then be readily acylated with any standard acylating agent to yield derivative 16 having a new C10 acyloxy substituent. Selective reduction of the C9 keto substituent of derivative 16 yields 9β-hydroxy derivative 17 to which a C13 side chain may be attached. Alternatively, the $C_{10}$ and C9 groups can be caused to migrate as set forth in Reaction Scheme 2, above.

treatment of the alcohol with a suitable base such as LDA followed by an acylating agent such as an acid chloride.

Baccatin III and 10-DAB analogs having different substituents at C2 and/or C4 can be prepared as set forth in Reaction Schemes 6–10. To simplify the description, 10-DAB is used as the starting material. It should be understood, however, that baccatin III derivatives or analogs may be produced using the same series of reactions (except for the protection of the C10 hydroxy group) by simply replacing 10-DAB with baccatin III as the starting material. Derivatives of the baccatin III and 10-DAB analogs having different substituents at C9 and at least one other position,

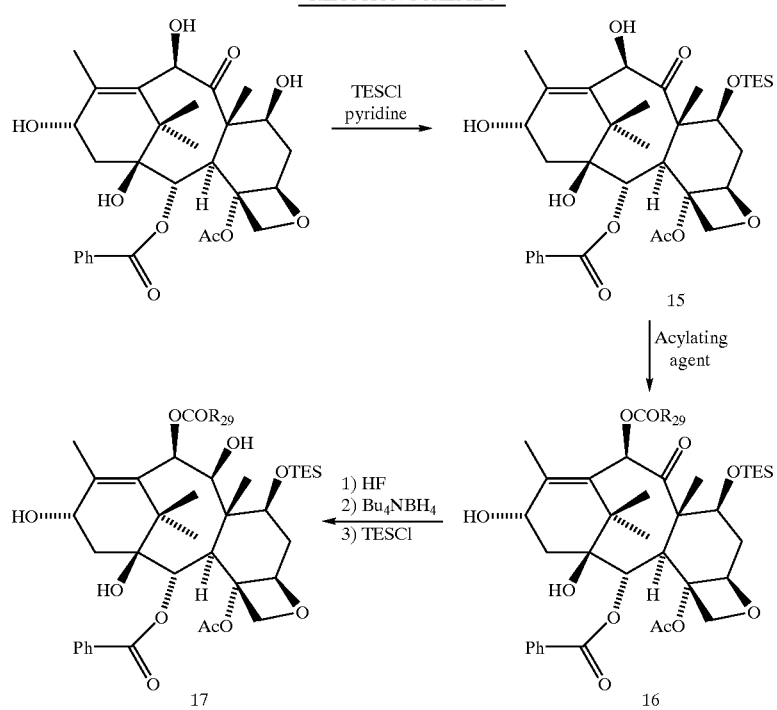

REACTION SCHEME 5

9-desoxo tetracyclic taxanes having alternative C2 and/or C4 esters can be prepared using baccatin III and 10-DAB as starting materials. The C2 and/or C4 esters of baccatin III and 10-DAB can be selectively reduced to the corresponding alcohol(s) using reducing agents such as LAH or Red-Al, and new esters can thereafter be substituted using standard acylating agents such as anhydrides and acid chlorides in combination with an amine such as pyridine, triethylamine, DMAP, or diisopropyl ethyl amine. Alternatively, the C2 and/or C4 alcohols may be converted to new C2 and/or C4 esters through formation of the corresponding alkoxide by for instance C1, C2, C4, C7, C10 and C13, can then be prepared by carrying out any of the other reactions described herein and any others which are within the level of skill in the art.

In Reaction Scheme 6, protected 10-DAB 3 is converted to the triol 18 with lithium aluminum hydride. Triol 18 is then converted to the corresponding C4 ester using $Cl_2CO$ in pyridine followed by a nucleophilic agent (e.g., Grignard reagents or alkyllithium reagents).

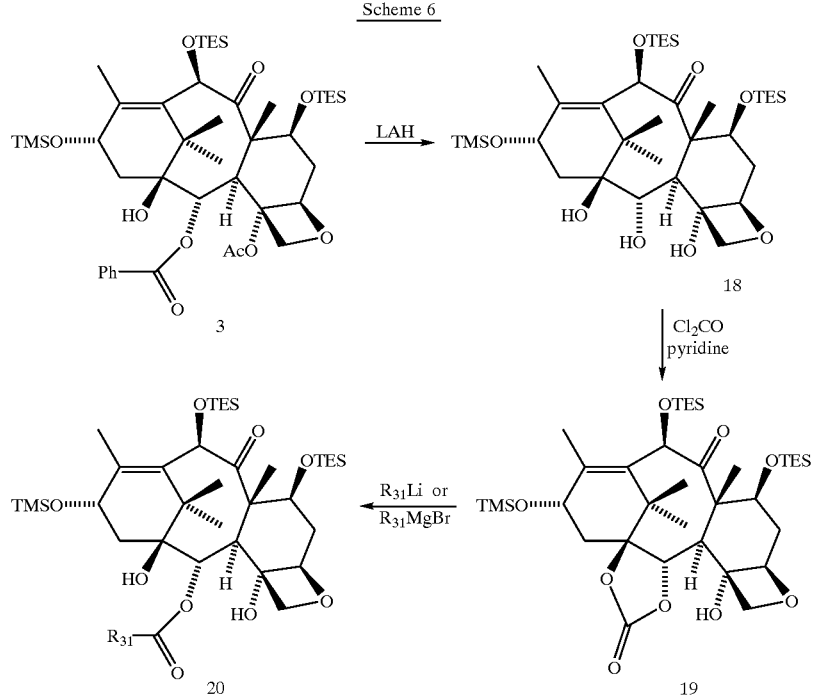

Deprotonation of triol 18 with LDA followed by introduction of an acid chloride selectively gives the C4 ester. For example, when acetyl chloride was used, triol 18 was converted to 1,2 diol 4 as set forth in Reaction Scheme 7.

Triol 18 can also readily be converted to the 1,2 carbonate 19. Acetylation of carbonate 19 under vigorous standard conditions provides carbonate 21 as described in Reaction Scheme 8; addition of alkyllithiums or Grignard reagents to carbonate 19 provides the C2 ester having a free hydroxyl group at C4 as set forth in Reaction Scheme 6.

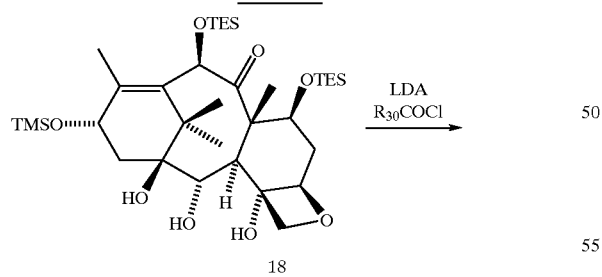

-continued

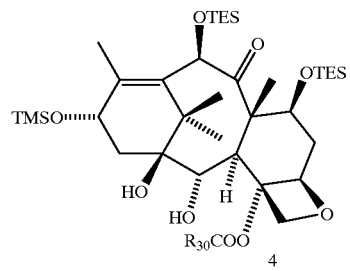

Scheme 8
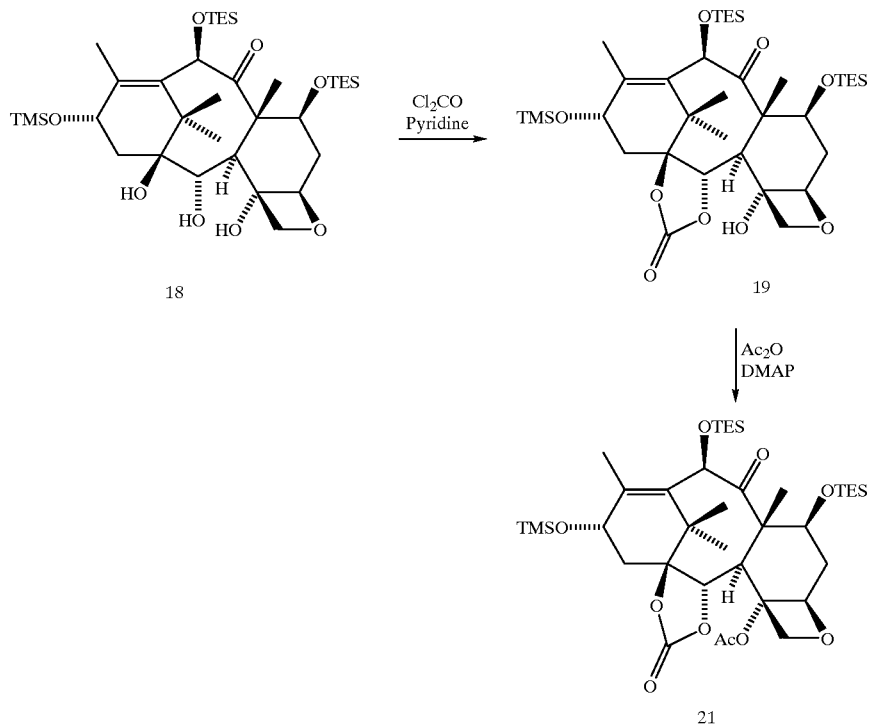
As set forth in Reaction Scheme 9, other C4 substituents can be provided by reacting carbonate 19 with an acid chloride and a tertiary amine to yield carbonate 22 which is then reacted with alkyllithiums or Grignard reagents to provide 10-DAB derivatives having new substituents at C2.
Scheme 9
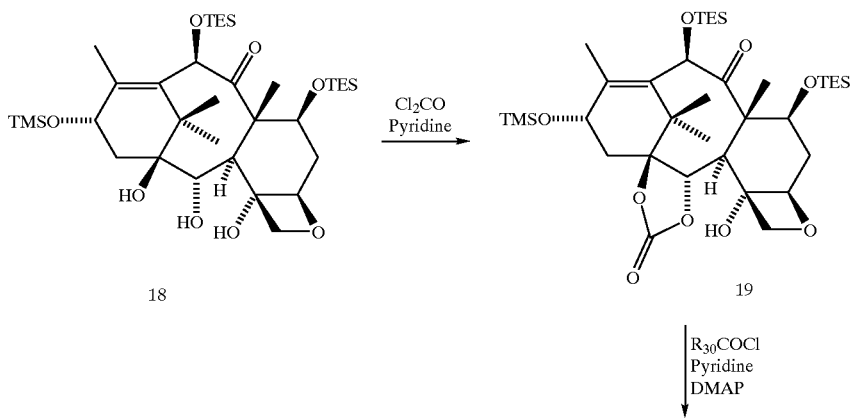

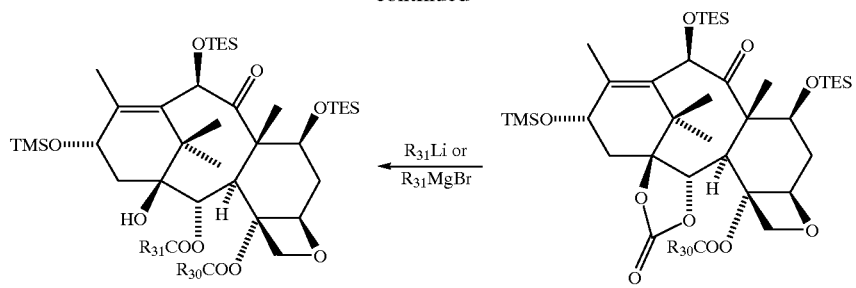

Alternatively, baccatin III may be used as a starting material and reacted as shown in Reaction Scheme 10. After being protected at C7 and C13, baccatin III is reduced with LAH to produce 1,2,4,10 tetraol 24. Tetraol 24 is converted to carbonate 25 using $Cl_2CO$ and pyridine, and carbonate 25 is acylated at C10 with an acid chloride and pyridine to produce carbonate 26 (as shown) or with acetic anhydride and pyridine (not shown). Acetylation of carbonate 26 under vigorous standard conditions provides carbonate 27 which is then reacted with alkyl lithiums to provide the baccatin III derivatives having new substituents at C2 and C10.

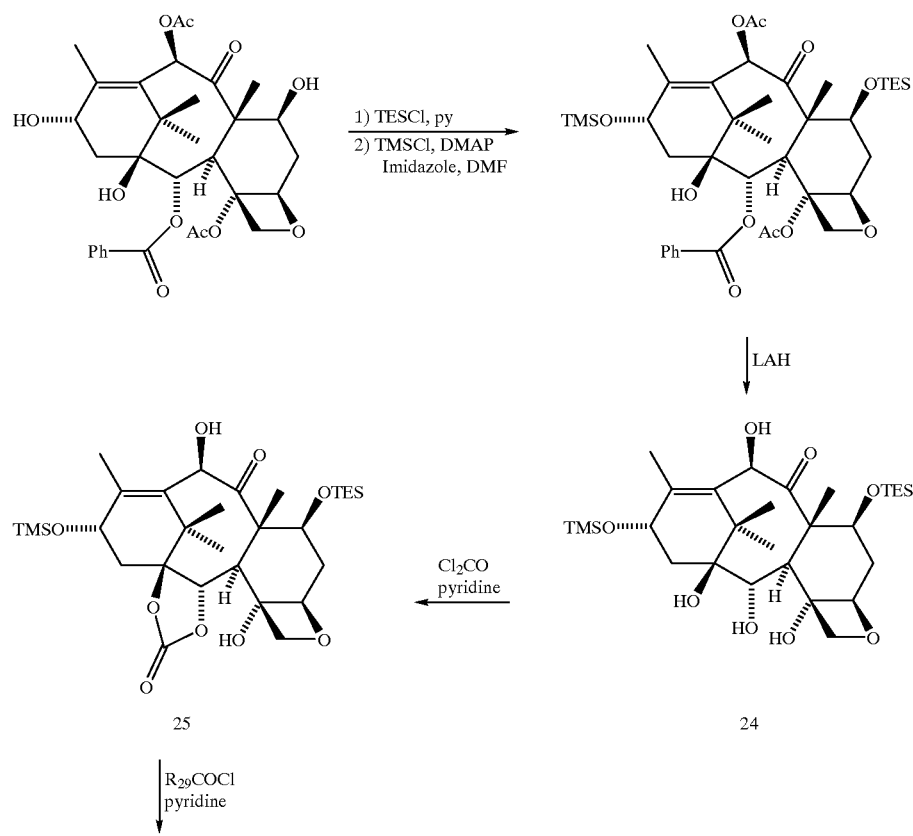

-continued

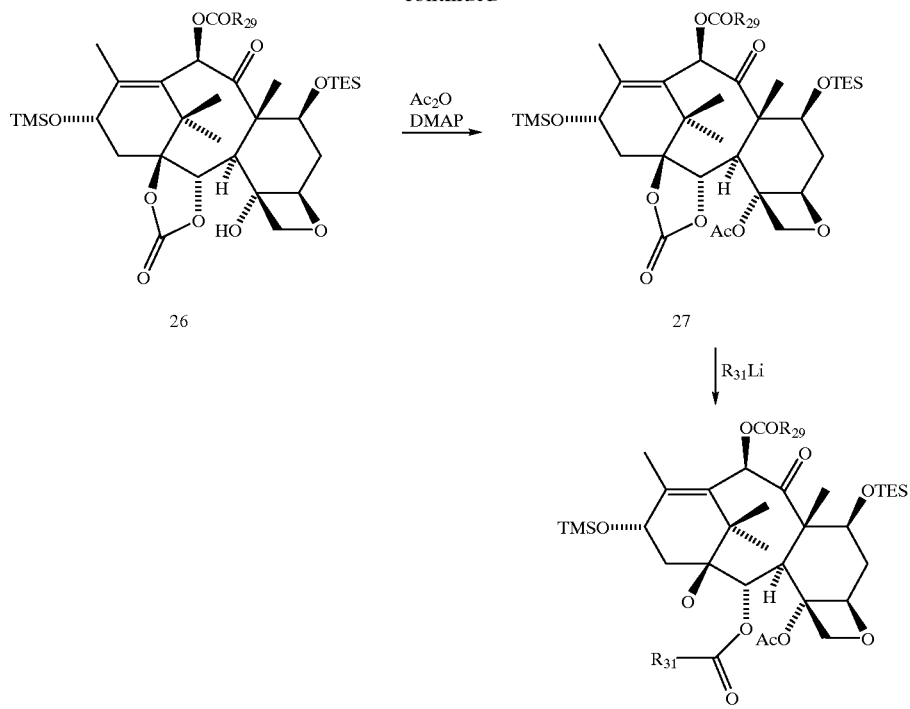

10-desacetoxy derivatives of baccatin III and 10-desoxy derivatives of 10-DAB may be prepared by reacting baccatin III or 10-DAB (or their derivatives) with samarium diiodide. Reaction between the tetracyclic taxane having a C10 leaving group and samarium diiodide may be carried out at 0° C. in a solvent such as tetrahydrofuran. Advantageously, the samarium diiodide selectively abstracts the C10 leaving group; C13 side chains and other substituents on the tetracyclic nucleus remain undisturbed. Thereafter, the C9 keto substituent may be reduced to provide the corresponding 9-desoxo-9β-hydroxy-10-desacetyoxy or 10-desoxy derivatives as otherwise described herein.

C7 dihydro and other C7 substituted taxanes can be prepared as set forth in Reaction Schemes 11, 12 and 12a.

REACTION SCHEME 11

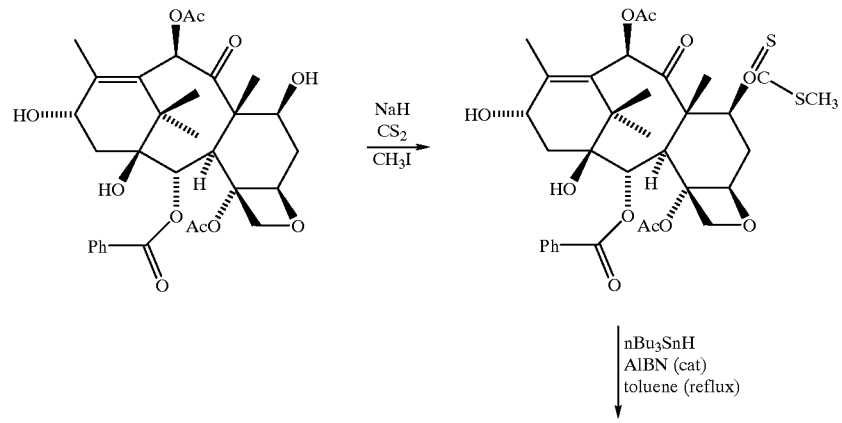

-continued
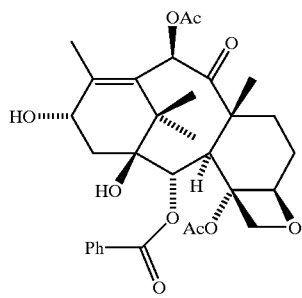
15
REACTION SCHEME 12
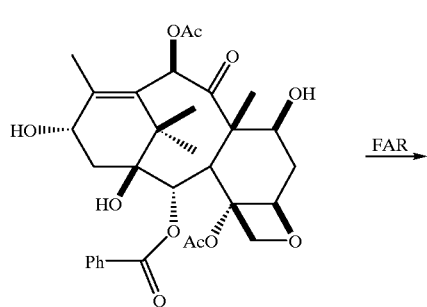
-continued
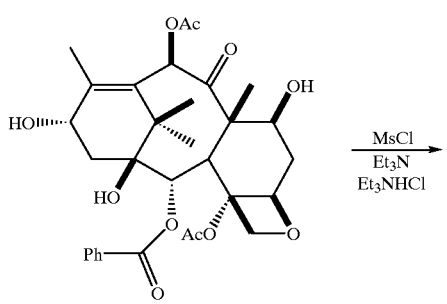
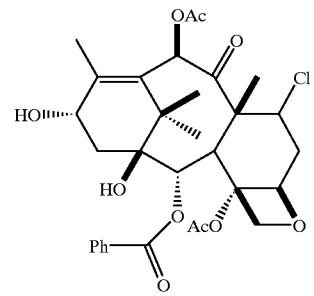
REACTION SCHEME 12a
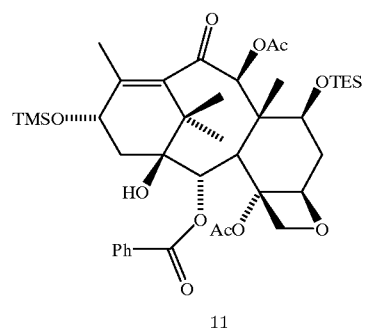
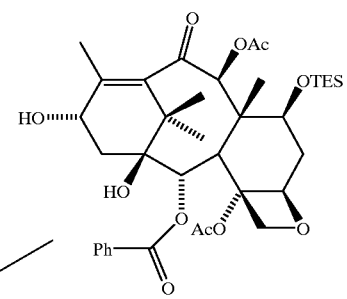

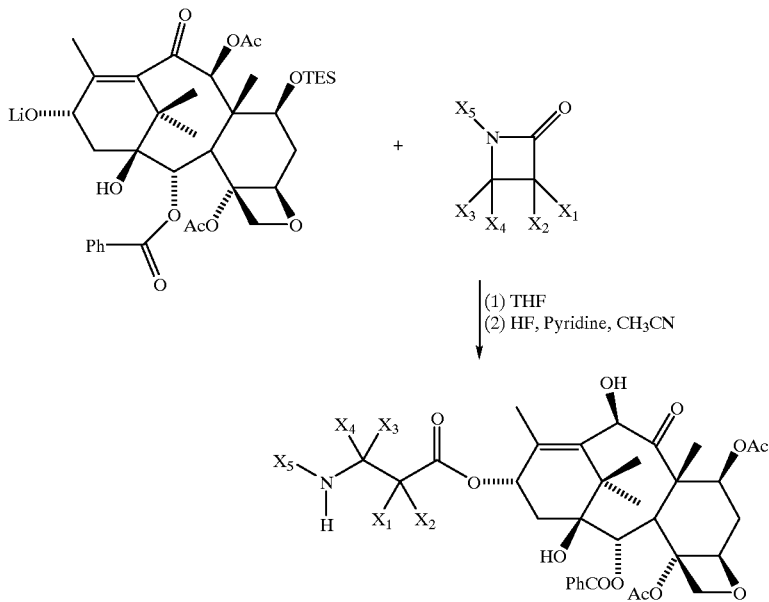

|(1) THF
|(2) HF, Pyridine, CH₃CN

As shown in Reaction Scheme 12, Baccatin III may be converted into 7-fluoro baccatin III by treatment with FAR at room temperature in THF solution. Other baccatin derivatives with a free C7 hydroxyl group behave similarly. Alternatively, 7-chloro baccatin III can be prepared by treatment of baccatin III with methane sulfonyl chloride and triethylamine in methylene chloride solution containing an excess of triethylamine hydrochloride.

Taxanes having C7 acyloxy substituents can be prepared as set forth in Reaction Scheme 12a, 7,13-protected 10-oxo-derivative 11 is converted to its corresponding C13 alkoxide by selectively removing the C13 protecting group and replacing it with a metal such as lithium. The alkoxide is then reacted with a β-lactam or other side chain precursor. Subsequent hydrolysis of the C7 protecting groups causes a migration of the C7 hydroxy substituent to $C_{10}$, migration of the C10 oxo substituent to C9, and migration of the C9 acyloxy substituent to C7.

A wide variety of tricyclic taxanes are naturally occurring, and through manipulations analogous to those described herein, an appropriate side chain can be attached to the C13 oxygen of these substances. Alternatively, as shown in Reaction Scheme 13, 7-O-triethylsilyl baccatin III can be converted to a tricyclic taxane through the action of trimethyloxonium tetrafluoroborate in methylene chloride solution. The product diol then reacts with lead tetraacetate to provide the corresponding C4 ketone.

REACTION SCHEME 13

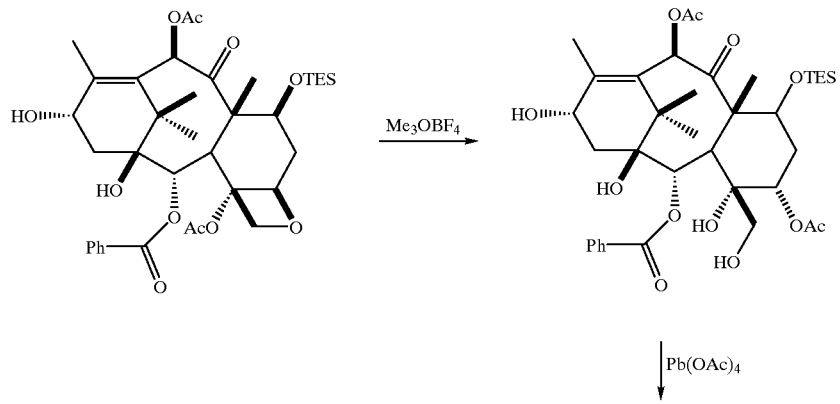

-continued

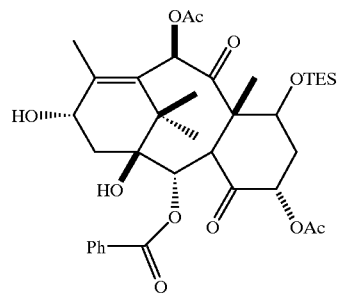

Recently a hydroxylated taxane (14-hydroxy-10-deacetylbaccatin III) has been discovered in an extract of yew needles (C&EN, p 36–37, Apr. 12, 1993). Derivatives of this hydroxylated taxane having the various C2, C4, etc. functional groups described above may also be prepared by using this hydroxylated taxane. In addition, the C14 hydroxy group together with the C1 hydroxy group of 10-DAB can be converted to a 1,2-carbonate as described in C&EN or it may be converted to a variety of esters or other functional groups as otherwise described herein in connection with the C2, C4, C9 and $C_{10}$ substituents.

The following examples are provided to more fully illustrate the invention.

EXAMPLE 1

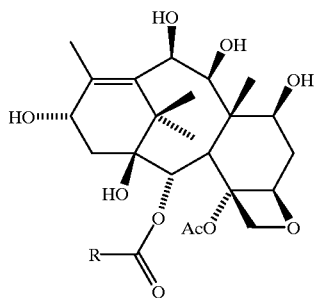

10-Deacetyl-9β-hydroxy-9-deoxo Baccatin (III)

A mixture of 10-deacetyl baccatin (III) (300 mg, 0.55 mmol) and n-$Bu_4NBH_4$ (709 mg, 2.76 mmol) in 50 mL of $CH_2Cl_2$ was stirred for 12 h at room temperature. The resulting mixture was diluted with ethyl acetate, and quenched by stirring with aqueous $NaHCO_3$ solution for 20 min. The organic layer was washed with aqueous $NaHCO_3$ and brine, dried over $Na_2SO_4$ and concentrated to give a residue which was purified by flash chromatography. Elution with ethyl acetate-methanol (50:1) afforded 256 mg (85%) of 10-deacetyl-9β-hydroxy-9-deoxo baccatin (III) which was recrystallized from $CH_2Cl_2$.

m.p. 209–210° C.; $[\alpha]^{25}$Na+14.67° (c 0.15, MeOH).

$^1$H NMR ($CD_3OD$, 500 MHz) δ8.11 (m, 2H, benzoate ortho), 7.61 (m, 1H, benzoate, para), 7.49 (m, 2H, benzoate, meta), 6.11 (d, J=5.5 Hz, 1H, H2), 5.09 (d, J=5.5 Hz, 1H, H10), 4.99 (d, J=8.5 Hz, 1H, H5), 4.80 (ddd, J=10.0, 6.0, 1.5 Hz, 1H, H13), 4.55 (d, J=5.5 Hz, 1H, H9α), 4.23 (d, J=8.0 Hz, 1H, H20α), 4.13 (dd, J=8.0, 1.0 Hz, 1H, H20β), 3.89 (dd, J=10.0, 7.0 Hz, 1H, H7), 3.23 (d, J=5.5 Hz, 1H, H3), 2.47 (ddd, J=15.0, 8.5, 7.0 Hz, 1H, H6α), 2.33 (dd, J=15.0, 6.0 Hz, 1H, H14α), 2.21 (s, 3H, 4Ac), 2.20 (ddd, J=15.0, 10.0, 1.0 Hz, 1H, H14β), 1.91 (d, J=1.5 Hz, 3H, Me18), 1.83 (ddd, J=15.0, 10.0, 1.0 Hz, 1H, H6β), 1.72 (s, 3H, Me16), 1.59 (s, 3H, Me19), 1.16 (s, 3H, Me17).

EXAMPLE 2

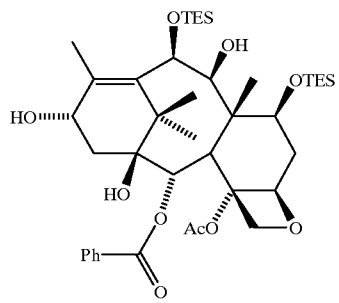

7,10-bis-O-Triethylsilyl-10-deacetyl-9β-hydroxy-9-deoxo Baccatin (III)

To a stirred solution of 10-deacetyl-9β-hydroxy-9-deoxo baccatin (III) (50 mg, 91.6 mmol) and triethylamine (128 mL, 916 mmol) in THF (0.35 mL) was added chlorotriethylsilane (185 mL, 641 mmol), and the reaction mixture was stirred for 24 h at room temperature. The resulting mixture was diluted with ethyl acetate and washed with aqueous $NaHCO_3$ and brine. The organic layer was dried over $Na_2SO_4$ and evaporated to give a residue, which was purified by flash chromatography. Elution with hexane-ethyl acetate (1:1) afforded 53 mg (75%) of 7,10-bis-O-triethylsilyl-10-deacetyl-9β-hydroxy-9-deoxo baccatin (III).

$^1$H NMR ($CDCl_3$, 500 MHz) δ8.11 (m, 2H, benzoate ortho), 7.57 (m, 1H, benzoate, para), 7.47 (m, 2H, benzoate, meta), 6.22 (d, J=5.0 Hz, 1H, H2), 5.03 (d, J=5.5 Hz, 1H, H10), 4.88 (d, J=8.7 Hz, 1H, H5), 4.81 (m, 1H, H13), 4.45 (d, J=5.5 Hz, 1H, H9α), 4.35 (d, J=8.2 Hz, 1H, H20α), 4.22 (d, J=8.2 Hz, 1H, H20β), 3.97 (dd, J=9.2, 7.8 Hz, 1H, H7), 3.15 (d, J=5.0 Hz, 1H, H3), 2.54 (m, 1H, H6α), 2.31 (dd, J=15.5, 10.5 Hz, 1H, H14) 2.29 (s, 3H, 4Ac), 2.01 (dd, J=15.5, 6.4 Hz, 1H, H14), 1.95 (d, J=1.5 Hz, 3H, Me18), 1.94 (m, 1H, H6β), 1.74 (s, 3H, Me16), 1.63 (s, 3H, Me19), 1.16 (s, 3H, Me17) 0.99 (m, 9H, triethylsilyl), 0.67 (m, 6H, triethylsilyl).

EXAMPLE 3

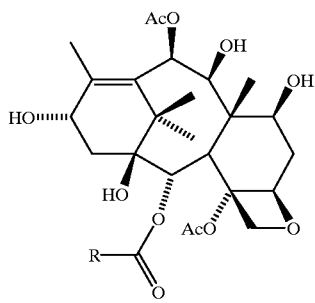

9β-Hydroxy-9-deoxo Baccatin III

To a solution of baccatin III (215 mg, 0.367 mmol) in 5 mL of $CH_2Cl_2$ was added n-$Bu_4NBH_4$ (944 mg, 3.67 mmol) and the mixture was stirred for 48 h at room temperature. The resulting mixture was diluted with ethyl acetate, and quenched by stirring with aqueous $NaHCO_3$ solution for 20 min. The organic layer was washed with aqueous $NaHCO_3$ and brine, dried over $Na_2SO_4$ and concentrated to give a residue which was separated by flash chromatography. Elution with $CH_2Cl_2$-acetone (2:1) afforded 111 mg (51%) of 9β-hydroxy-9-deoxo baccatin (III), which was recrystallized from ethyl acetate-ether-hexane.

m.p. 160–162° C.; $[α]^{25}Na$ –3.6° (c 0.055, $CHCl_3$).

$^1H$ NMR ($CDCl_3$, 500 MHz) δ8.11 (m, 1H, benzoate ortho), 7.59 (m, 1H, benzoate, para), 7.47 (m, 2H, benzoate, meta), 6.20 (d, J=5.0 Hz, 1H, H2β), 6.16 (d, J=5.5 Hz, 1H, H10), 4.95 (d, J=6.5 Hz, 1H, H5), 4.82 (dd, J=8.5, 7.0 Hz, 1H, H13), 4.44 (d, J=5.0 Hz, 1H, H9), 4.37 (d, J=8.0 Hz, 1H, H20α), 4.21 (d, J=8.0 Hz, 1H, H20α), 4.08 (br t, J=8.0 Hz, 1H, H7), 3.18 (d, J=5.0 Hz, 1H, H3), 2.55 (ddd, J=15.0, 8.0, 7.0 Hz, 1H, H6α), 2.32 (ddd, J=15.5, 10.0, 1.0 Hz, 1H, H14β), 2.30 (s, 3H, 4Ac), 2.16 (s, 3H, 10Ac), 2.09 (d, J=1.5 Hz, 3H, Me18), 2.04 (dd, J=15.5, 6.5 Hz, 1H, H14α), 1.90 (ddd, J=15.0, 9.0, 2.0 Hz, 1H, H6α), 1.69 (s, 3H, Me16), 1.66 (s, 3H, Me19), 1.11 (s, 3H, Me17).

EXAMPLE 4

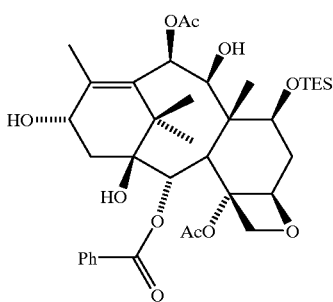

7-O-Triethylsilyl-9β-hydroxy-9-deoxo Baccatin (III)

To a To a solution of triethylamine (0.330 mL, 2.35 mmol) in THF (36 mL) at 0° C. was added triethylsilyl chloride (0.39 mL, 2.35 mmol). To this mixture was added a solution of 9β-hydroxy-9-deoxo baccatin (III) (276 mg, 0.47 mmol) in 10 mL of THF. The solution was warmed to room temperature and stirred for 49 h. MeOH (1 mL) was added and the mixture was stirred for 10 min. The resulting solution was poured into saturated aqueous $NaHCO_3$ (100 mL) and extracted with ethyl acetate (2×150 mL). The organic layer was washed with saturated aqueous $NaHCO_3$ (100 mL) and brine (100 mL), dried over $Na_2SO_4$, filtered, and concentrated under reduced pressure to give a crude residue (0.3 g). Flash column chromatography ($CH_2Cl_2$-ethyl acetate) afforded 7-O-triethylsilyl-9β-hydroxy-9-deoxo baccatin (III) (297 mg, 89%).

$^1H$-NMR ($CDCl_3$, 500 Mz), δ8.11 (dd, J=1, 7.5 Hz, 2H benzoate ortho), 7.56–7.59 (m, 1H, benzoate), 7.45–7.48 (m, 2H, benzoate), 6.20 (d, J=5 Hz, 1H, H-2), 6.16 (d, J=5.5 Hz, 1H, H10), 4.88 (d, J=9 Hz, 1H, H-5),4.84 (m, 1H, H-13), 4.63 (br-d, J=6 Hz, 1H, H-9), 4.36 (d, J=9 Hz, 1H, H-20α), 4.20 (d, J=9 Hz, 1H, H-20β), 3.93 (dd, J=7, 8.5 Hz, 1H, H-7), 3.19 (d, J=5 Hz, 1H, H-3), 2.63 (br-d, J=4 Hz, 1H, OH-9), 2.51 (m, 1H, H-6α), 2.47 (d, J=6 Hz, 1H, OH-10), 2.32 (dd, J=10, 16 Hz, 1H, H-14β), 2.29 (s, 3H, Ac), 2.21 (d, J=9 Hz, 1H, OH-13), 2.17 (s, 1H, OH-1), 2.03 (m, 1H, H-14α), 1.98 (d, J=1.5 Hz, 3H, Me-18), 1.93 (ddd, J=1.5, 9.5 15 Hz, 1H, H-6β), 1.74 (s, 3H, Me-16), 1.63 (s, 3H, Me-19), 1.17 (s, 3H, Me-17), 0.99 (t, J=7.5 Hz, 9H, SiCH2CH3), 0.63 and 0.64 (q×2, J=7.5 Hz, 6H, SiCH2CH3).

EXAMPLE 5

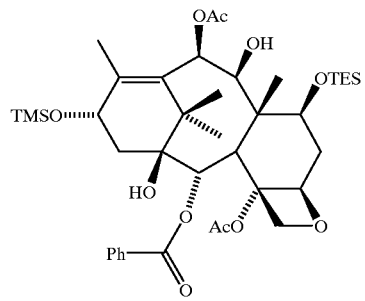

7-O-Triethylsilyl-9β-hydroxy-9-deoxo-13-O-trimethylsilyl Baccatin (III)

To a stirred solution of 7-O-triethylsilyl-9β-deoxo baccatin (III) (140 mg; 0.196 mmol) in anhydrous pyridine (0.7 mL) at room temperature TMSCl (0.24 mL; 1.9 mmol) was added. After stirring for 36 h the reaction mixture was diluted with ethyl acetate (50 mL) and the mixture was poured into saturated aqueous $NaHCO_3$ (25 mL). The organic phase was washed with saturated aqueous $NaHCO_3$ and brine, dried over $Na_2SO_4$ and evaporated. The product was isolated by filtration through a small pad of $Sio_2$ eluting with 15% EA-hexanes affording 140 mg (94%) of 7-O-triethylsilyl-9β-hydroxy-9-deoxo-13-O-trimethylsilyl baccatin (III).

$^1H$-nmr (300 MHz, $CDCl_3$) δ8.10 (dd; 2H; J=7.7, 1.1 Hz; o-Bz); 7.58 (t; 1H; J=7.7 Hz; p-Bz); 7.46 (br t; 2H; J=7.7 Hz; m-Bz); 6.12 (d; 1H; J=5.0 Hz; H-2β); 6.10 (d; 1H; J=3.8 Hz; H-10α); 5.00 (br t; 1H; J=8.2 Hz; H-13β); 4.93 (d; 1H; J=8.8 Hz; H-5α); 4.58 (br d; 1H; J=3.8 Hz; H-9α); 4.33 (d; 1H;J=8.2 Hz; H-20α); 4.14 (d; 1H; J=8.2 Hz; H-20β); 4.01 (dd; 1H; J=8.8, 7.7 Hz; H-7α); 3.12 (d; 1H; J=5.0 Hz; H-3α); 2.53 (ddd; 1H; J=14.8, 8.8, 7.7 Hz; H-6a); 2.23 (s; 3H; 4-OAc); 2.21 (br s; 1H; 9-OH); 2.20 (dd; 1H; J=14.0, 8.2 Hz; H-14a); 2.11 (s; 3H; 10-OAc); 2.07 (dd; 1H; J=14.0, 8.2 Hz; H-14β); 2.04 (br s; 3H; 18-Me); 1.89 (brdd; 1H; J=14.8, 9.9 Hz; H-6β); 1.76 (s; 1H; 1-OH); 1.74 (s; 3H; 16-Me); 1.59 (s, 3H; 19-Me); 1.19 (s, 3H; 17-Me); 0.95 (t; 9H; J=8.0 Hz; 7-TES-Me): 0.65 (m; 6H; TES-$CH_2$); 0.01(s, 9H; TMS).

EXAMPLE 6

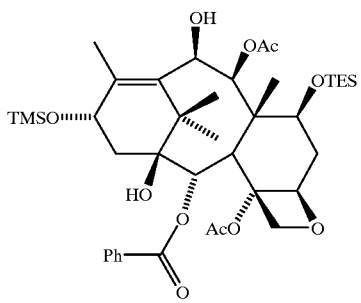

7-O-Triethylsilyl-9β-acetoxy-9-deoxo-10-deacetyl-13-O-trimethylsilyl Baccatin (III)

To a stirred suspension of KH (250 mg, 35% in mineral oil, washed 3×1 mL with pentane; 2.19 mmol) in anhydrous THF (2.5 mL) a solution of 7-O-triethyl-silyl-9β-hydroxy-9-deoxo-13-O-trimethylsilyl baccatin (III) (142 mg; 0.18 mmol) in anhydrous THF (4 mL) was added at 0° C. After 5 min the mixture was warmed up to room temperature and stirred for 30 min and then cooled down to −10° C. The reaction mixture was quenched with AcOH in THF solution (1.6M; 0.15 mL) and stirred for 5 min at the same temperature before diluting with ethyl acetate (50 mL). The mixture was poured into saturated aqueous NaHCO$_3$ (50 mL) and the organic phase was washed with brine, dried over Na$_2$SO$_4$ and evaporated. The product was isolated by flash chromatography (SiO$_2$; 25% ethyl acetate-hexanes) affording 29 mg of recovered starting material (21%) and 107 mg (75%) of 7-O-triethylsilyl-9β-acetoxy-9-deoxo-10-deacetyl-13-O-trimethylsilyl baccatin (III). $^1$H-nmr (500 MHz, CDCl$_3$) δ 8.10 (br dd; 2H; J=7.3, 1.1 Hz; o-Bz); 7.59 (tt; 1H; J=7.3, 1.3 Hz; p-Bz); 7.43 (br t; 2H; J=7.3 Hz; m-Bz); 6.09 (d; 1H; J=5.9 Hz; H-9α); 6.04 (br d; 1H; J=4.8 Hz; H-2β); 5.25 (dd; 1H; J=5.9, 1.5 Hz; H-10α); 5.05 (br t; 1H; J=8.6 Hz; H-13β); 4.92 (br d; 1H; J=8.8 Hz; H-5α); 4.32 (br d; 1H;J=8.4 Hz; H-20α); 4.09 (dd; 1H; J=8.4, 0.7 Hz; H-20β); 4.02 (dd; 1H; J=9.2, 7.7 Hz; H-7α); 3.23 (br d; 1H; J=4.8 Hz; H-3α); 2.56 (ddd; 1H; J=15.0, 9.5, 7.7 Hz; H-6α); 2.26 (s; 3H; 9-OAc); 2.24 (s; 3H; 4-OAc); 2.21 (dd; 1H; J=15.0, 7.7 Hz; H-14α); 2.16 (d; 1H; J=1.5 Hz; 10-OH); 2.12 (br dd; 1H; J=15.0, 9.7 Hz; H-14β); 1.93 (d; 3H; J=1.1 Hz; 18-Me); 1.89 (brdd; 1H; J=15.0, 9.2, 1.1 Hz; H-6β); 1.715 (s; 3H; 16-Me); 1.71 (s; 1H; 1-OH); 1.42 (s, 3H; 19-Me); 1.28 (s, 3H; 17-Me); 1.02 (t; 9H; J=8.0 Hz; TES-Me); 0.68 (m; 6H; TES-CH$_2$); 0.01 (s, 9H; TMS).

EXAMPLE 7

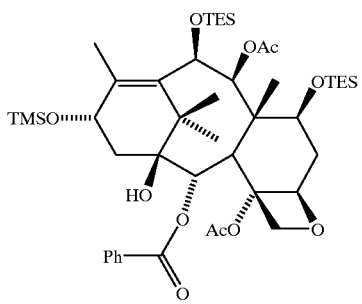

7,10-bis-O-Triethylsilyl-9β-acetoxy-9-deoxo-10-deacetyl-13-O-trimethylsilyl Baccatin (III)

To a solution of 7-O-triethylsilyl-9β-hydroxy-9-deoxo-13-O-trimethylsilyl baccatin (III) (72 mg; 0.09 mmol) and triethylamine (128 mL, 916 mmol) in THF (0.35 mL) was added chlorotriethylsilane (185 mL, 641 mmol), and the reaction mixture was stirred for 24 h at room temperature. The resulting mixture was diluted with ethyl acetate and washed with aqueous NaHCO$_3$ and brine. The organic layer was dried over Na$_2$SO$_4$ and concentrated to give a residue, which was purified by flash chromatography. Elution with hexane-ethyl acetate (1:1) afforded 63 mg (75%) of 7,10-bis-O-triethylsilyl-9β-acetoxy-9-deoxo-10-deacetyl-13-O-trimethylsilyl Baccatin (III).

$^1$H-nmr (500 MHz, CDCl$_3$) δ 8.10 (br dd; 2H; J=7.3, 1.1 Hz; o-Bz); 7.59 (tt; 1H; J=7.3, 1.3 Hz; p-Bz); 7.43 (br t; 2H; J=7.3 Hz; m-Bz); 6.09 (d; 1H; J=5.9 Hz; H-9α); 6.04 (br d; 1H; J=4.8 Hz; H-2β); 5.10 (d; 1H; J=5.5; H-10α); 5.05 (br t; 1H; J=8.6 Hz; H-13β); 4.92 (br d; 1H; J=8.8 Hz; H-5α); 4.32 (br d; 1H;J=8.4 Hz; H-20α); 4.09 (dd; 1H; J=8.4, 0.7 Hz; H-20β); 4.02 (dd; 1H; J=9.2, 7.7 Hz; H-7α); 3.23 (br d; 1H; J=4.8 Hz; H-3α); 2.56 (ddd; 1H; J=15.0, 9.5, 7.7 Hz; H-6α); 2.26 (s; 3H; 9-OAc); 2.24 (s; 3H; 4-OAc); 2.21 (dd; 1H; J=15.0, 7.7 Hz; H-14α); 2.12 (br dd; 1H; J=15.0, 9.7 Hz; H-14β); 1.93 (d; 3H; J=1.1 Hz; 18-Me); 1.89 (brdd; 1H; J=15.0, 9.2, 1.1 Hz; H-6β); 1.715 (s; 3H; 16-Me); 1.71 (s; 1H; 1-OH); 1.42 (s, 3H; 19-Me); 1.28 (s, 3H; 17-Me); 1.02 (t; 9H; J=8.0 Hz; TES-Me); 0.68 (m; 6H; TES-CH$_2$); 0.01 (s, 9H; TMS).

EXAMPLE 8

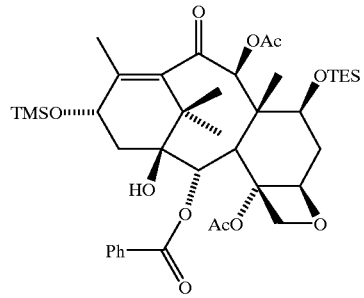

7-O-Triethylsilyl-9β-acetoxy-9-deoxo-10-deacetoxy-10-oxo-13-O-trimethylsilyl Baccatin (III)

A suspension of 7-O-triethylsilyl-9β-acetoxy-9-deoxo-10-deacetyl-13-O-trimethylsilyl baccatin (III) (47 mg; 0.06 mmol), NMO (9 mg; 0.077 mmol) and powdered 4A molecular sieves (25 mg) in anhydrous CH$_2$Cl$_2$ (2.5 mL) was stirred at room temperature for 5 minutes and then a catalytic amount of TPAP was added (1 mg approx.). The mixture was stirred for 1h and then filtered through a small pad of coarse SiO$_2$ eluting with 20% ethyl acetate-hexanes. The filtrate was evaporated affording 45.5 mg (97%) of 7-O-Triethylsilyl-9β-acetoxy-9-deoxo-10-deacetoxy-10-oxo-13-O-trimethylsilyl baccatin (III).

$^1$H-nmr (500 MHz, CDCl$_3$) δ8.16 (br dd; 2H; J=8.2, 1.2 Hz; o-Bz); 7.61 (br tt; 1H; J=7.3, 1.2 Hz; p-Bz); 7.49 (br t; 2H; J=8.0 Hz; m-Bz); 5.84 (d; 1H; J=5.1 Hz; H-2β); 5.26 (2; 1H; H-9α); 5.00 (br s; 1H; w½=8 Hz; H-5α); 4.98 (br t; 1H; J=8.2 Hz; H-13β); 4.43 (dd; 1H; J=7.6, 1.0 Hz, H-20β); 4.23 (dd; 1H;J=7.6, 1.0 Hz; H-20α); 4.23 (br overlapped; 1H; H-7α); 3.57 (br d; 1H; J=5.1 Hz; H-3α); 2.32 (dd; 1H; J=14.9, 7.6 Hz; H-14α); 2.31 (s; 3H; 4-OAc); 2.24 (s; 3H; 9-OAc); 2.17 (br dd; 1H; J=14.9, 8.9 Hz; H-14β); 2.07 (d; 3H; J=1.3 Hz; 18-Me); 2.04 (ddd; 1H; J=14.9, 3.6, 2.3 Hz; H-6b); 1.97 (ddd; 1H; J=14.9, 3.3, 2.4 Hz; H-6α); 1.79 (s; 1H; 1-OH); 1.44 (s; 3H; 19-Me); 1.32 (s, 3H; 16-Me); 1.25 (s, 3H; 17-Me); 0.93 (t; 9H; J=8.0 Hz; 7-TES-Me); 0.59 (c; 6H; 7-TES-CH$_2$); 0.01 (s, 9H; TMS).

EXAMPLE 9

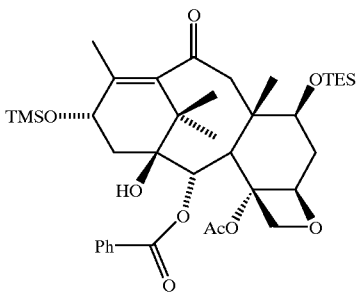

7-O-Triethylsilyl-9-deoxo-10-deacetoxy-10-oxo-13-O-trimethylsilyl Baccatin (III)

To a stirred solution of 7-O-triethylsilyl-9β-acetoxy-9-deoxo-10-deacetoxy-10-oxo-13-O-trimethylsilyl baccatin (III) (14 mg; 0.018 mmol) in anhydrous THF (0.2 mL) a solution of SmI$_2$ in THF (0.1M; 1 mL) was added under nitrogen at room temperature and the resulting solution was stirred for 1.5 h. The reaction mixture was opened to the air to quench the excess Sm(II), diluted with ethyl acetate (20 mL) and the mixture was poured into ice cold 0.2N HCl and extracted with ethyl acetate; the organic phase was washed with 5% aqueous citric acid, saturated aqueous NaHCO$_3$ and brine, dried over Na$_2$SO$_4$ and evaporated. The product was isolated by flash chromatography (SiO$_2$; 15% ethyl acetate-hexanes) affording 10 mg (81%) of 7-O-triethylsilyl-9-deoxo-10-deacetoxy-10-oxo-13-O-trimethylsilyl baccatin (III).

$^1$H-nmr (300 MHz, CDCl$_3$) δ8.13 (br d; 2H; J=7.5 Hz; o-Bz); 7.62 (br t; 1H; J=7.5 Hz; p-Bz); 7.49 (br t; 2H; J=7.5 Hz; m-Bz); 5.89 (d; 1H; J=6.0 Hz; H-2β); 4.97 (br t; 1H; J=7.8 Hz; H-13β); 4.91 (d; 1H; J=8.0 Hz; H-5α); 4.33 (br d; 1H;J=8.0 Hz; H-20α); 4.14 (d; 1H; J=8.0 Hz; H-20β); 3.79 (dd; 1H; J=9.0, 6.6 Hz; H-7α); 3.34 (d; 1H; 16.5 Hz; H-9); 3.15 (d; 1H; J=6.0 Hz; H-3α); 2.57 (d; 1H; 16.5 Hz; H-9); 2.49 (ddd; 1H; J=16.5, 9.0, 8.0 Hz; H-6α); 2.25 (s; 3H; 4-OAc); 2.18 (m; 2H; H-14); 1.82 (br s, 3H; 18-Me); 1.75 (ddd; 1H; J=16.5, 6.6, 1.8 Hz; H-6β); 1.72 (s; 1H; 1-OH); 1.48 (s; 3H; Me); 1.38 (s, 3H; Me); 1.23 (s, 3H; Me); 0.99 (t; 9H; J=8.0 Hz; TES-Me); 0.65 (m; 6H; TES-CH$_2$); 0.01 (s, 9H; TMS).

EXAMPLE 10

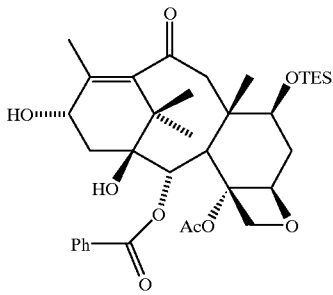

7-O-Triethylsilyl-9-deoxo-10-deacetoxy-10-oxo Baccatin (III)

To a solution of 7-O-triethylsilyl-9-deoxo-10-deacetoxy-10-oxo-13-O-trimethylsilyl baccatin (III). (30 mg, 0.025 mmol) in 2.25 mL of acetonitrile and 2.25 mL of THF in a polyethylene vial was added dropwise 0.048 mL of pyridine and 0.075 mL of 48% aqueous HF. The reaction mixture was stirred at room temperature for 12 h and then diluted with ethyl acetate (20 mL). Saturated aqueous sodium bicarbonate was added and the organic layer was separated, washed with brine, dried over anhydrous sodium sulfate and concentrated to give a crude residue. Flash chromatography with 25% ethyl acetate in hexane gave 22 mg (80%) of 7-O-triethylsilyl-9-deoxo-10-deacetoxy-10-oxo baccatin (III).

$^1$H-nmr (300 MHz, CDCl$_3$) δ8.13 (br d; 2H; J=7.5 Hz; o-Bz); 7.62 (br t; 1H; J=7.5 Hz; p-Bz); 7.49 (br t; 2H; J=7.5 Hz; m-Bz); 5.89 (d; 1H; J=6.0 Hz; H-2β); 4.97 (br t; 1H; J=7.8 Hz; H-13β); 4.91 (d; 1H; J=8.0 Hz; H-5α); 4.33 (br d; 1H;J=8.0 Hz; H-20α); 4.14 (d; 1H; J=8.0 Hz; H-20β); 3.79 (dd; 1H; J=9.0, 6.6 Hz; H-7α); 3.34 (d; 1H; 16.5 Hz; H-9); 3.15 (d; 1H; J=6.0 Hz; H-3α); 2.57 (d; 1H; 16.5 Hz; H-9); 2.49 (ddd; 1H; J=16.5, 9.0, 8.0 Hz; H-6α); 2.25 (s; 3H; 4-OAc); 2.18 (m; 2H; H-14); 1.82 (br s, 3H; 18-Me); 1.75 (ddd; 1H; J=16.5, 6.6, 1.8 Hz; H-6β); 1.72 (s; 1H; 1-OH); 1.48 (s; 3H; Me); 1.38 (s, 3H; Me); 1.23 (s, 3H; Me); 0.99 (t; 9H; J=8.0 Hz; TES-Me); 0.65 (m; 6H; TES-CH$_2$).

EXAMPLE 11

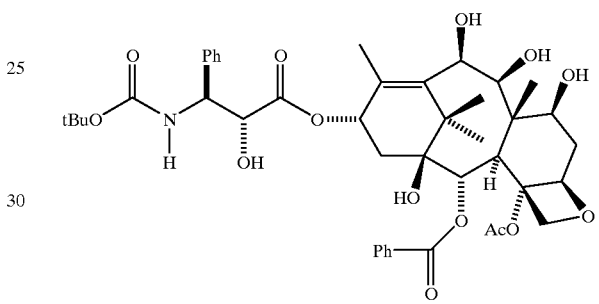

(67-3) Preparation of 10-Deacetyl-9-desoxo-9β-hydroxy-N-debenzoyl-N-(t-butoxycarbonyl)taxol To a solution of 7,10-(bis)triethylsilyl-10-deacetyl-9-desoxo-9β-hydroxy baccatin III (95 mg, 0.123 mmol) in 1 mL of THF at −45° C. was added dropwise 0.250 mL of a 0.98M solution of (TMS)2NLi in THF. After 1 h at −45° C., a solution of cis-1-(t-butoxycarbonyl)-3-triethylsilyloxy-4-phenylazetidin-2-one (137 mg, 0.37 mmol) in 1 mL of THF was added dropwise to the mixture. The solution was gradually warmed to 0° C. during 6 h before 1 mL of aqueous solution was added. The mixture was partitioned between saturated aqueous NaHCO$_3$ and ethyl acetate. Evaporation of the organic layer gave a residue which was purified by flash chromatography to afford 127 mg of (2'R,3'S)-2',7,10-(tris)triethylsilyl-10-deacetyl-9-desoxo-9β-hydroxy-N-debenzoyl-N-(t-butoxycarbonyl) taxol and 8 mg of the (2'S,3'R) isomer.

To a solution of 90 mg of the major compound obtained from the previous reaction in 1.5 mL of acetonitrile and 2 mL of pyridine at 0° C. was added 0.8 mL of 48% aqueous HF. The mixture was stirred at 0° C. for 3 h, then at 25° C. for 24 h, and partitioned between saturated aqueous sodium bicarbonate and ethyl acetate. Evaporation of the ethyl acetate solution gave 71 mg of material which was purified by flash chromatography to give 58 mg (92%) of 10-deacetyl-9-desoxo-9β-hydroxy-N-debenzoyl-N-(t-butoxycarbonyl)taxol, which was recrystallized from ethyl acetate/ether/hexane.

m.p. 160–161° C.; [α]$^{25}$Na −18.75° (c 0.08, CHCl$_3$).

$^1$H NMR (CD$_3$OD, 500 MHz) δ8.10 (d, J=7.0 Hz, 2H, benzoate ortho), 7.61 (m, 1H, benzoate, para), 7.50 (m, 2H, benzoate, meta), 7.41 (d, J=8.0 Hz, 2H, phenyl, ortho), 7.36 (m, 2H, phenyl, meta), 7.28 (m, 1H, phenyl, para),6.18 (m, 1H, H13), 6.18 (d, J=5.5 Hz, 1H, H2β), 5.18 (br s, 1H, H3'), 5.10 (d, J=5.5 Hz, 1H, H10), 4.99 (d, J=8.2 Hz, 1H, H5), 4.91 (d, J=9.3 Hz, 1H, NH), 4.59 (br s, 1H, H2'), 4.51 (d, J=5.5 Hz, 1H, H9), 4.22(d, J=8.0 Hz, 1H, H20α), 4.16 (d, J=8.0 Hz, 1H, H20β), 3.86 (dd, J=9.5, 7.5 Hz, 1H, H7), 3.13 (d, J=5.5 Hz, 1H, H3), 2.48 (m, 1H, H6α), 2.29 (m, 1H, H14α), 2.28 (s, 3H, 4Ac), 2.19 (m , 1H, H14β), 1.85 (ddd, J=15.1, 9.6, 1.4 Hz, 1H, H6β), 1.79 (s, 3H, Me16), 1.78 (s, 3H, Me18), 1.61 (s, 3H, Me19H), 1.42 (s, 9H, t-Bu), 1.29 (s, 3H, Me17).

EXAMPLE 12

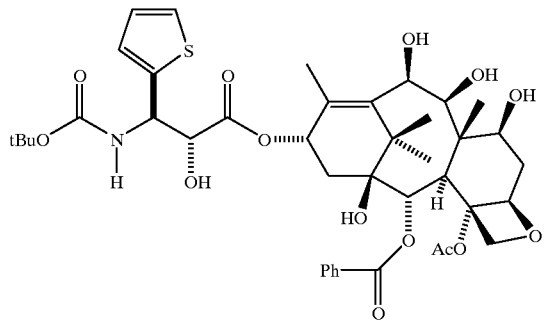

(70-2)
Preparation of 3'-Desphenyl-3'-(2-thienyl)-N-desbenzoyl-N-(t-butoxycarbonyl)-9-desoxo-9β-hydroxy-10-desacetyl Taxol To a solution of 7,10-(bis)-O-triethylsilyl-9-desoxo-9β-hydroxy-10-deacetyl baccatin (III) (70.0 mg, 0.09 mmol) in 1.0 mL of THF at −45° C. was added dropwise 0.10 mL of a 0.98 M solution of LiN(SiMe$_3$)$_2$ in hexane. After 0.5 h at −45° C., a solution of cis-1-t-butoxycarbonyl-3-triethylsilyloxy-4-(2-thienyl)azetidin-2-one (103.8 mg, 0.27 mmol) in 1.0 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 97.4 mg of a mixture containing (2'R,3'S)-2',7,10-(tris)-O-triethylsilyl-3'-desphenyl-3'-(2-thienyl)-N-desbenzoyl-N-(t-butoxycarbonyl)-9-desoxo-9β-hydroxy-10-desacetyl taxol and a small amount of the (2'S,3'R) isomer.

To a solution of 97.4 mg (0.084 mmol) of the mixture obtained from the previous reaction in 13.5 mL of acetonitrile and 0.57 mL of pyridine at 0° C. was added 1.92 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 69.4 mg of material which was purified by flash chromatography to give 63.1 mg (89%) of 3'-desphenyl-3'-(2-thienyl)-N-desbenzoyl-N-(t-butoxycarbonyl)-9-desoxo-9β-hydroxy-10-desacetyl taxol, which was recrystallized from methanol/water.

m.p. 146–148° C.; [α]$^{25}$Na −54.2° (c 0.0026, CHCl$_3$)

$^1$H NMR (MeOH, 300 MHz) δ8.11(d, J=7.1 Hz, 2H, benzoate ortho), 7.61(m, 1H, benzoate para), 7.48(m, 2H, benzoate meta), 7.25(dd, J=5.4, 1.2 Hz, 1H, thienyl), 7.14(d, J=3.3 Hz, 1H, thienyl), 7.03(dd, J=5.4, 3.9 Hz, 1H, thienyl), 6.18(m, 1H, H13), 6.18(d, J=5.5 Hz, 1H, H2), 5.23(br s, 1H, H3'), 5.07(d, J=5.5 Hz, 1H, H10), 4.97(d, J=8.1 Hz, 1H, H5), 4.84(d, J=9.3 hz, 1H, NH), 4.52(br s, 1H, H2'), 4.50(d, J=5.5 Hz, 1H, H9), 4.23(d, J=8.1, 1H, H20α), 4.16(d, J=8.1 Hz, 1H, H20β), 3.92(dd, J=9.4, 7.5 Hz, 1H, H7), 3.13(d, J=5.5 Hz, H3), 2.47(m, 1H, H6α), 2.26(m, 1H, H14α), 2.27(s, 3H, 4Ac), 2.16(m, 1H, H14β), 1.84(ddd, J=15.1, 9.4, 1.2 Hz, H6β), 1.79(s, 3H, Me16), 1.76(s, 3H, Me18), 1.62(s, 3H, Me19) 1.39(s, 9H, 3Me t-butoxy), 1.27(s, 3H, Me17).

EXAMPLE 13

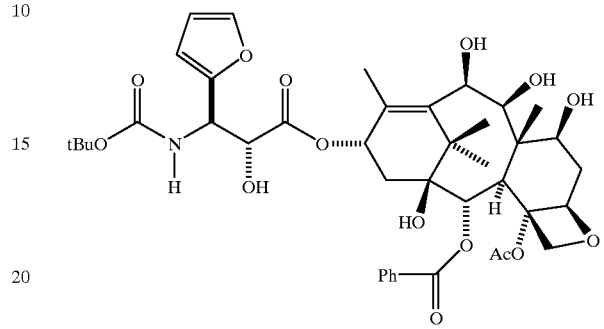

(70-3)
Preparation of 3'-Desphenyl-3'-(2-furyl)-N-desbenzoyl-N-(t-butoxycarbonyl)-9-desoxo-9β-hydroxy-10-desacetyl Taxol To a solution of 7,10-(bis)-O-triethylsilyl-9-desoxo-9β-hydroxy-10-deacetyl baccatin (III) (70.0 mg, 0.09 mmol) in 1.0 mL of THF at −45° C. was added dropwise 0.10 mL of a 0.98 M solution of LiN(SiMe$_3$)$_2$ in hexane. After 0.5 h at −45° C., a solution of cis-1-t-butoxycarbonyl-3-triethylsilyloxy-4-(2-furyl)azetidin-2-one (99.5 mg, 0.27 mmol) in 1.0 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 94.3 mg of a mixture containing (2'R,3'S)-2',7,10-(tris)-O-triethylsilyl-3'-desphenyl-3'-(2-furyl)-N-desbenzoyl-N-(t-butoxycarbonyl)-9-desoxo-9β-hydroxy-10-desacetyl taxol and a small amount of the (2'S,3'R) isomer.

To a solution of 94.3 mg (0.082 mmol) of the mixture obtained from the previous reaction in 13.5 mL of acetonitrile and 0.57 mL of pyridine at 0° C. was added 1.92 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution crave 72.3 mg of material which was purified by flash chromatography to give 59.1 mg (89%) of 3'-desphenyl-3'-(2-furyl)-N-desbenzoyl-N-(t-butoxycarbonyl)-9-desoxo-9β-hydroxy-10-desacetyl taxol, which was recrystallized from methanol/water.

m.p. 144–146° C.; [α]$^{25}$Na −54.0° (c 0.0028, CHCl$_3$).

$^1$H NMR (MeOH, 300 MHz) δ8.10(d, J=7.1 Hz, 2H, benzoate ortho), 7.60(m, 1H, benzoate para), 7.51(m, 2H, benzoate meta), 7.40(m, 1H, furyl), 6.37(m, 1H, furyl), 6.34(m, 1H, furyl), 6.17(m, 1H, H13), 6.16(d, J=5.4 Hz, 1H, H2), 5.24(br s., 1H, H3'), 5.11(d, J=5.5 Hz, 1H, H10), 4.86(d, J=8.1 Hz, 1H, H5), 4.83(d, J=9.3 hz, 1H, NH), 4.50(d, J=5.5 Hz, 1H, H9), 4.45(br s, 1H, H2'), 4.21(d, J=8.1, 1H, H20α), 4.13(d, J=8.1 Hz, 1H, H20β), 3.92(dd, J=9.4, 7.5 Hz, 1H, H7), 3.11(d, J=5.5 Hz, H3), 2.46(m, 1H, H6α), 2.24(m, 1H, H14α), 2.21(s, 3H, 4Ac), 2.15(m, 1H, H14β), 1.79(ddd, J=15.1, 9.4, 1.2 Hz, H6β), 1.77(s, 3H, Me16), 1.73(s, 3H, Me18), 1.61(s, 3H, Me19), 1.37(s, 9H, 3Me t-buthoxy), 1.26(s, 3H, Me17).

EXAMPLE 14

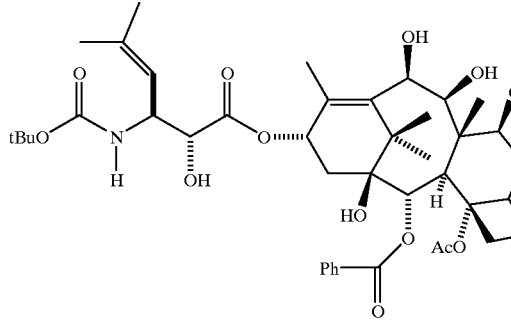

(70-4)

Preparation of 3'-Desphenyl-3'-(isobutenyl)-N-desbenzoyl-N-(t-butoxycarbonyl)-9-desoxo-9β-hydroxy-10-desacetyl Taxol To a solution of 7,10-(bis)-O-triethylsilyl-9-desoxo-9β-hydroxy-10-deacetyl baccatin (III) (70.0 mg, 0.09 mmol) in 1.0 mL of THF at −45° C. was added dropwise 0.10 mL of a 0.98 M solution of LiN(SiMe$_3$)$_2$ in hexane. After 0.5 h at −45° C., a solution of cis-1-(t-butoxycarbonyl)-3-(2-methoxyisopropyloxy)-4-(isobutenyl)azetidin-2-one (84.5 mg, 0.27 mmol) in 1.0 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 88.3 mg of a mixture containing (2'R,3'S)-2',7,10-(tris)-O-triethylsilyl-3'-desphenyl-3'-(isobutenyl)-N-desbenzoyl-N-(t-butoxycarbonyl)-9-desoxo-9β-hydroxy-10-desacetyl taxol and a small amount of the (2'S,3'R) isomer.

To a solution of 88.3 mg (0.080 mmol) of the mixture obtained from the previous reaction in 13.5 ml, of acetonitrile and 0.55 mL of pyridine at 0° C. was added 1.90 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 67.2 mg of material which was purified by flash chromatography to give 52.7 mg (82%) of 3'-desphenyl-3'-(isobutenyl)-N-desbenzoyl-N-(t-butoxycarbonyl)-9-desoxo-9β-hydroxy-10-desacetyl taxol, which was recrystallized from methanol/water.

m.p. 138–140° C.; [α]$^{25}$Na −55.2° (c 0.0026, CHCl$_3$).

$^1$H NMR (MeOH, 300 MHz) δ8.11(d, J=7.1 Hz, 2H, benzoate ortho), 7.61(m, 1H, benzoate para), 7.48(m, 2H, benzoate meta), 6.13(m, 1H, H13), 6.12(m, 1H, H2), 5.21(br s., 1H, H3'), 5.02(d, J=5.3 Hz, 1H, H10), 4.93(d, J=8.1 Hz, 1H, H5), 4.85(d, J=9.1 hz, 1H, NH), 4.84(d, J=8.5 Hz, 1H, Me$_2$C=CH—), 4.50(br s, 1H, H2'), 4.50(d, J=5.5 Hz, 1H, H9), 4.22(d, J=8.1, 1H, H20α), 4.18(d, J=8.1 Hz, 1H, H20β), 3.89(dd, J=9.4, 7.5 Hz, 1H, H7), 3.12(d, J=5.5 Hz, H3), 2.45(m, 1H, H6α), 2.31(m, 1H, H14α), 2.29(s, 3H, 4Ac), 2.18(m, 1H, H14β), 1.85(ddd, J=15.1, 9.4, 1.2 Hz, H6β), 1.81(s, 3H, Me16), 1.76(s, 3H, Me18), 1.72(s, 6H, 2Me from isobuthenyl), 1.61(s, 3H, Me19), 1.39(s, 9H, 3Me t-buthoxy), 1.26(s, 3H, Me17).

EXAMPLE 15

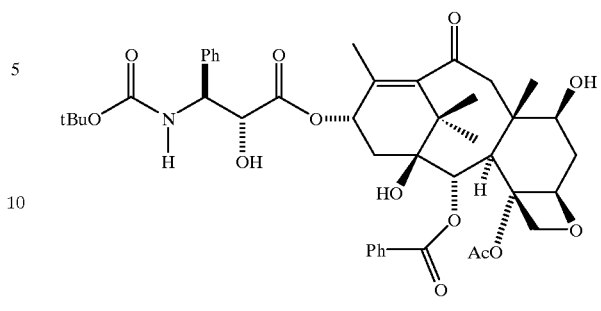

(74-3)

Preparation of N-desbenzoyl-N-(t-butoxycarbonyl)-9-desoxo-10-desacetoxy-10-keto Taxol To a solution of 7-O-triethylsilyl-9-desoxo-10-desacetoxy-10-keto baccatin (III) (30.0 mg, 0.047 mmol) in 0.5 mL of THF at −45° C. was added dropwise 0.05 mL of a 0.98 M solution of LiN(SiMe$_3$)$_2$ in hexane. After 0.5 h at −45° C., a solution of cis-1-t-butoxycarbonyl-3-triethylsilyloxy-4-phenylazetidin-2-one (53.1 mg, 0.14 mmol) in 0.5 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 43.7 mg of a mixture containing (2'R,3'S)-2',7-(bis)-O-triethylsilyl-N-desbenzoyl-N-(t-butoxycarbonyl)-9-desoxo-10-desacetoxy-10-keto taxol and a small amount of the (2'S,3'R) isomer.

To a solution of 43.7 mg (0.042 mmol) of the mixture obtained from the previous reaction in 4.0 mL of acetonitrile and 0.20 mL of pyridine at 0° C. was added 0.50 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 33.2 mg of material which was purified by flash chromatography to give 24.1 mg (73%) of N-desbenzoyl-N-(t-butoxycarbonyl)-9-desoxo-10-desacetoxy-10-keto taxol, which was recrystallized from methanol/water.

m.p. 162–165° C.; [α]$^{25}$Na −58.7° (c 0.0025, CHCl$_3$).

$^1$H NMR (CDCl$_3$, 300 MHz) δ8.11(d, J=7.1 Hz, 2H, benzoate ortho), 7.63(m, 1H, benzoate para), 7.50(m, 2H, benzoate meta), 7.40–7.29(m, 5H, benzoate, phenyl), 6.11 (td, J=7.8, 1.0 Hz, 1H, H13), 5.94(d, J=6.4 Hz, 1H, H2), 5.52(d, J=9.8 Hz, 1H, H3'), 5.27(d, J=9.3 Hz, 1H, NH), 4.93(dd, J=8.8 Hz, 1H, H5), 4.64(br s, 1H, H2'), 4.32(d, J=8.3 Hz, 1H, H20α), 4.18(d, J=8.3 Hz, 1H, H20β), 3.88(br s, 1H, 2'OH), 3.71(m, 1H, H7), 3.11(d, J=5.1 Hz, 1H, H3), 3.10(d, J=15.7 Hz, H9α), 2.88(d, J=16.1, 1H, H9β), 2.54(m, 1H, H6α), 2.44(m, 1H, H14β), 2.29(s, 3H, 4Ac), 2.26(mn, 1H, H14α), 2.02(br s, 1H, 7 OH), 1.88(s, 1H, 1 OH), 1.80(m, 1H, H6β), 1.65(s, 3H, Me18), 1.55(s, 3H, Me16), 1.46(s, 3H, Me19), 1.35(s, 9H, 3Me t-butoxy), 1.29(s, 3H, Me17) .(74-4)

EXAMPLE 16

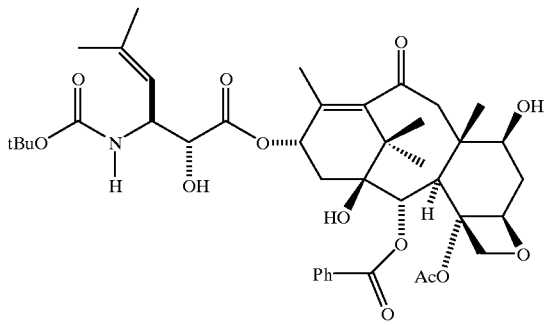

(74-4)
Preparation of 3'-Desphenyl-3'-(isobutenyl)-N-desbenzoyl-N-(t-butoxycarbonyl)-9-desoxo-10-desacetoxy-10-keto Taxol To a solution of 7-O-triethylsilyl-9-desoxo-10-desacetoxy-10-keto baccatin (III) (30.0 mg, 0.047 mmol) in 0.5 mL of THF at −45° C. was added dropwise 0.05 mL of a 0.98 M solution of LiN(SiMe$_3$)$_2$ in hexane. After 0.5 h at −45° C., a solution of cis-1-t-butoxycarbonyl-3-(2-methoxyisopropyloxy)-4-(isobutenyl)azetidin-2-one (44.1 mg, 0.141 mmol) in 0.5 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 40.8 mg of a mixture containing (2'R,3'S)-2'-O-(2-methoxyisopropyl)-7-O-triethylsilyl-3'-desphenyl-3'-(isobutenyl)-N-desbenzoyl-N-(t-butoxycarbonyl)-9-desoxo-10-desacetoxy-10-keto taxol and a small amount of the (2'S,3'R) isomer.

To a solution of 40.8 mg (0.043 mmol) of the mixture obtained from the previous reaction in 4 mL of acetonitrile and 0.2 mL of pyridine at 0° C. was added 0.5 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 34.4 mg of material which was purified by flash chromatography to give 23.0 mg (70%) of 3'-desphenyl-3'-(isobutenyl)-N-desbenzoyl-N-(t-butoxycarbonyl)-9-desoxo-10-desacetoxy-10-keto taxol, which was recrystallized from methanol/water.

m.p. 149–153° C.; [α]$^{25}$Na −56.3° (c 0.0025, CHCl$_3$).

$^1$H NMR (CDCl$_3$, 300 MHz) δ8.12(d, J=7.2 Hz, 2H, benzoate ortho), 7.64(m, 1H, benzoate para), 7.51(m, 2H, benzoate meta), 6.12(t, J=7.5 Hz, 1H, H13), 5.95(d, J=6.2 Hz, 1H, H2), 5.30(d, J=8.9 Hz, 1H, NH), 4.94(d, J=8.2 Hz, 1H, H5), 4.88(d, J=8.9 Hz, 1H, Me$_2$C=CH—), 4.79(td, J=8.9, 2.4 Hz, 1H, H3'), 4.34(d, J=8.2 Hz, 1H, H20α), 4.27(dd, J=5.5, 2.7 Hz, 1H, H2'), 4.19(d, J=8.2 Hz, 1H, H20α), 3.73(m, 1H, H7), 3.67(br s, 1H, 2'OH), 3.13(d, J=5.1 Hz, 1H, H3), 3.12(d, J=15.7 Hz, 1H, H9α), 2.90(d, J=15.7 Hz, 1H, H9β), 2.55(m, 1H, H6α), 2.47(m, 1H, H14β), 2.32(s, 3H, 4Ac), 2.28(m, 1H, H14α), 2.04(br s, 1H, 7 OH), 1.88(s, 1H, 1 OH), 1.82(m, 1H, H6β), 1.79(s, 3H, Me18), 1.76(s, 6H, 2Me from isobuthenyl), 1.57(s, 3H, Me16), 1.47 (s, 3H, Me19), 1.40(s, 9H, 3Me t-buthoxy) 1.30(s, 3H, Me17).(75-1)

EXAMPLE 17

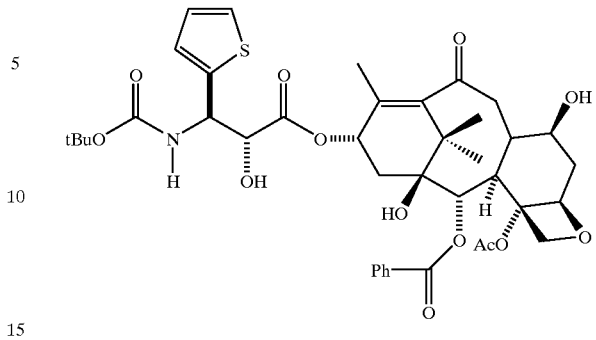

(75-1)
Preparation of 3'-Desphenyl-3'-(2-thienyl)-N-desbenzoyl-N-(t-butoxycarbonyl)-9-desoxo-10-desacetoxy-10-keto Taxol To a solution of 7-O-triethylsilyl-9-desoxo-10-desacetoxy-10-keto baccatin (III) (25.0 mg, 0.039 mmol) in 0.5 mL of THF at −45° C. was added dropwise 0.05 mL of a 0.98 M solution of LiN(SiMe$_3$)$_2$ in hexane. After 0.5 h at −45° C., a solution of cis-1-t-butoxycarbonyl-3-triethylsilyloxy-4-(2-thienyl)azetidin-2-one (45.0 mg, 0.117 mmol) in 0.5 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO, and 60/40 ethyl acetate/hexane. Evaporation of the organic layer gave a residue which was purified by filtration through silica gel to give 36.2 mg of a mixture containing (2'R,3'S)-2',7-(bis)-O-triethylsilyl-3'-desphenyl-3'-(2-thienyl)-N-desbenzoyl-N-(t-butoxycarbonyl)-9-desoxo-10-desacetoxy-10-keto taxol and a small amount of the (2'S,3'R) isomer.

To a solution of 36.2 mg (0.035 mmol) of the mixture obtained from the previous reaction in 3.0 mL of acetonitrile and 0.15 mL of pyridine at 0° C. was added 0.45 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 29.4 mg of material which was purified by flash chromatography to give 24.3 mg (87%) of 3'-desphenyl-3'-(2-thienyl)-N-desbenzoyl-N-(t-butoxycarbonyl)-9-desoxo-10-desacetoxy-10-keto taxol, which was recrystallized from methanol/water.

m.p. 163–169° C.; [α]$^{25}$Na −54.2° (c 0.0023, CHCl$_3$).

$^1$H NMR (CDCl$_3$, 300 MHz) δ8.12(d, J=7.3 Hz, 2H, benzoate ortho), 7.64(m, 1H, benzoate para), 7.51(m, 2H, benzoate meta), 7.26(m, 1H, thienyl), 7.10(d, J=3.4 Hz, 1H, thienyl), 6.99(dd, J=5.1, 3.4 Hz, 1H, thienyl), 6.12(td, J=6.1, 1.0 Hz, 1H, H13), 5.95(d, J=5.9 Hz, 1H, H2), 5.50(d, J=4.4 Hz, 1H, NH), 5.42(d, J=9.8 Hz, 1H, H3'), 4.94(d, J=8.3 Hz, 1H, H5), 4.64(dd, J=4.2, 2.0 Hz, 1H, 2'), 4.33(d, J=7.8 Hz, 1H, H20α), 4.18(d, J=7.8 Hz, 1H, H20β), 3.90(br s, 1H, 2'OH), 3.73(m, 1H, H7), 3.11(d, J=15.8 Hz, H9α), 3.09(d, J=5.1 Hz, 1H, H3), 2.90(d, J=15.6 Hz, 1H, H9β), 2.54(m, 1H, H6α), 2.45(m, 1H, H14β), 2.31(s, 3H, 4Ac), 2.28(m, 1H, H14α), 2.01(br s, 1H, 7 OH), 1.88(s, 1H, 1 OH), 1.83(m, 1H, H6β), 1.69(s, 3H, Me18), 1.56(s, 3H, Me16), 1.46(s, 3H, Me19), 1.40(s, 9H, 3Me t-buthoxy), 1.29(s, 3H, Me17).

EXAMPLE 18

Taxanes 67-3, 70-2, 70-3, 70-4, 75-1, 74-4, and 74-3 of Examples 11–17 were evaluated in in vitro cytotoxicity activity against human colon carcinoma cells HCT-116. Cytotoxicity was assessed in HCT116 human colon carcinoma cells by XTT (2,3-bis(2-methoxy-4-nitro-5-sulfophenyl)-5-[(phenyl-amino)carbonyl]-2H-tetrazolium hydroxide) assay (Scudiero et al, "Evaluation of a soluble tetrazolium/formazan assay for cell growth and drug sensitivity in culture using human and other tumor cell lines", *Cancer Res.* 48:4827–4833, 1988). Cells were plated at 4000 cells/well in 96 well microtiter plates and 24 hours later drugs were added and serial diluted. The cells were incubated at 37° C. for 72 hours at which time the tetrazolium dye, XTT, was added. A dehydrogenase enzyme in live cells reduces the XTT to a form that absorbs light at 450 nm which can be quantitated spectrophotometrically. The greater the absorbance the greater the number of live cells. The results are expressed as an $IC_{50}$ which is the drug concentration required to inhibit cell proliferation (i.e. absorbance at 450 nm) to 50% of that of untreated control cells.

All compounds had an $IC_{50}$ less than 0.1, indicating that they are all cytotoxically active.

What we claim is:

1. A tetracyclic taxane having the formula

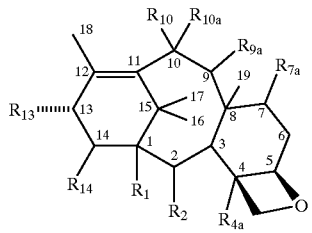

wherein $R_1$ is hydrogen, hydroxy, protected hydroxy or together with $R_{14}$ forms a carbonate;

$R_2$ is hydrogen, hydroxy, or —$OCOR_{31}$;

$R_{4a}$ is hydrogen, alkyl, alkenyl, hydroxy, or —$OCOR_{30}$;

$R_{7a}$ is hydrogen, halogen, or —$OR_{28}$;

$R_{9a}$ is β-hydroxy, β-protected hydroxy, or β-acyloxy;

$R_{10}$ is hydrogen or together with $R_{10a}$ forms an oxo;

$R_{10a}$ is hydrogen, —$OCOR_{29}$, hydroxy or protected hydroxy, or together with $R_{10}$ forms an oxo;

$R_{13}$ is hydroxy or protected hydroxy;

$R_{14}$ is hydrogen, hydroxy, protected hydroxy, or together with $R_1$ forms a carbonate;

$R_{28}$ is hydrogen, acyl, or hydroxy protecting group; and $R_{29}$, $R_{30}$ and $R_{31}$ are independently hydrogen, alkyl, alkenyl, alkynyl, monocyclic aryl or monocyclic heteroaryl.

2. A tetracyclic taxane having the formula

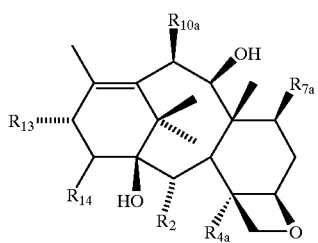

wherein $R_2$ is hydrogen, hydroxy, or —$OCOR_{31}$;

$R_{4a}$ is hydrogen, alkyl, alkenyl, hydroxy, or —$OCOR_{30}$;

$R_{7a}$ is hydrogen, halogen or —$OR_{28}$;

$R_{10a}$ is hydrogen, —$OCOR_{29}$, hydroxy or protected hydroxy;

$R_{13}$ is hydroxy or protected hydroxy;

$R_{14}$ is hydrogen, hydroxy, or protected hydroxy;

$R_{28}$ is hydrogen, acyl, or hydroxy protecting group; and $R_{29}$, $R_{30}$ and $R_{31}$ are independently hydrogen, alkyl, alkenyl, alkynyl, monocyclic aryl or monocyclic heteroaryl.

3. The taxane of claim 1 wherein $R_{9a}$ is, β-hydroxy or β-acyloxy.

4. The taxane of claim 1 wherein $R_{9a}$ is β-acyloxy.

5. The taxane of claim 1 wherein $R_{9a}$ is β-hydroxy or β-protected hydroxy.

6. The taxane of claim 1 wherein $R_2$ is —$OCOR_{31}$, and $R_{31}$ is as defined in claim 1.

7. The taxane of claim 1 wherein $R_{4a}$ is —$OCOR_{30}$, and $R_{30}$ is as defined in claim 1.

8. The taxane of claim 1 wherein $R_{7a}$ is hydroxy or protected hydroxy.

9. The taxane of claim 1 wherein $R_{10a}$ is —$OCOR_{29}$, and $R_{29}$ is as defined in claim 1.

10. The taxane of claim 1 wherein $R_1$ is hydroxy; $R_2$ is —$OCOR_{31}$; $R_{4a}$ is —$OCOR_{30}$; $R_{7a}$ is hydroxy or protected hydroxy; $R_{10a}$ is —$OCOR_{29}$; $R_{14}$ is hydrogen; $R_{29}$ and $R_{30}$ are alkyl; and $R_{31}$ is aryl.

11. The taxane of claim 10 wherein $R_{9a}$ is, β-hydroxy, β-protected hydroxy, or β-acyloxy.

12. The taxane of claim 2 wherein $R_2$ is —$OCOR_{31}$ and $R_{31}$ is as defined in claim 2.

13. The taxane of claim 2 wherein $R_{4a}$ is —$OCOR_{30}$ and $R_{30}$ is as defined in claim 2.

14. The taxane of claim 2 wherein $R_{7a}$ is hydroxy or protected hydroxy.

15. The taxane of claim 2 wherein $R_{10a}$ is —$OCOR_{29}$, and $R_{29}$ is as defined in claim 2.

16. The taxane of claim 2 wherein $R_2$ is —$OCOR_{31}$; $R_{4a}$ is —$OCOR_{30}$; $R_{10a}$ is —$OCOR_{29}$; $R_{14}$ is hydrogen; $R_{29}$ and $R_{30}$ are alkyl; and $R_{31}$ is aryl.

17. The taxane of claim 16 wherein $R_{4a}$ and $R_{10a}$ are acetoxy, and $R_2$ is benzoyloxy.

18. A tetracyclic taxane having the formula

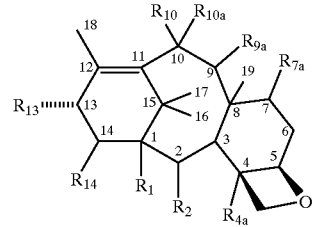

wherein $R_1$ is hydroxy, protected hydroxy or together with $R_{14}$ forms a carbonate;

$R_2$ is hydroxy, or —$OCOR_{31}$;

$R_{4a}$ is hydroxy, or —$OCOR_{30}$;

$R_{7a}$ is halogen, or —$OR_{28}$;

$R_{9a}$ is β-hydroxy, β-protected hydroxy or β-acyloxy;

$R_{10}$ is hydrogen;

$R_{10a}$ is —$OCOR_{29}$, hydroxy or protected hydroxy, or together with $R_{10}$ forms an oxo;

$R_{13}$ is hydroxy or protected hydroxy;

$R_{14}$ is hydrogen, hydroxy, protected hydroxy, or together with $R_1$ forms a carbonate;

$R_{28}$ is hydrogen, acyl, or hydroxy protecting group; and $R_{29}$, $R_{30}$ and $R_{31}$ are independently hydrogen, alkyl, alkenyl, alkynyl, monocyclic aryl or monocyclic heteroaryl.

19. The taxane of claim 18 wherein $R_2$ is —OCOR$_{31}$ and $R_{31}$ is as defined in claim 18.

20. The taxane of claim 18 wherein $R_{4a}$ is —OCOR$_{30}$ and $R_{30}$ is as defined in claim 18.

21. The taxane of claim 18 wherein $R_{7a}$ is hydroxy or protected hydroxy.

22. The taxane of claim 18 wherein $R_{10a}$ is —OCOR$_{29}$, and $R_{29}$ is as defined in claim 18.

23. The taxane of claim 18 wherein $R_2$ is —OCOR$_{31}$; $R_{4a}$ is —OCOR$_{30}$; $R_{10a}$ is —OCOR$_{29}$; $R_{14}$ is hydrogen; $R_{29}$ and $R_{30}$ are alkyl; and $R_{31}$ is aryl.

24. The taxane of claim 16 wherein $R_{4a}$ and $R_{10a}$ are acetoxy, and $R_2$ is benzoyloxy.

25. A tetracyclic taxane having the formula

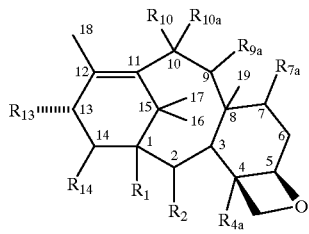

wherein $R_1$ is hydroxy, protected hydroxy or together with $R_{14}$ forms a carbonate;

$R_2$ is —OCOR$_{31}$;

$R_{4a}$ is —OCOR$_{30}$;

$R_{7a}$ is —OR$_{28}$;

$R_{9a}$ is β-hydroxy, β-protected hydroxy or β-acyloxy;

$R_{10}$ is hydrogen;

$R_{10a}$ is —OCOR$_{29}$, hydroxy or protected hydroxy;

$R_{13}$ is hydroxy or protected hydroxy;

$R_{14}$ is hydrogen;

$R_{28}$ is hydrogen, acyl, or hydroxy protecting group; and $R_{29}$, $R_{30}$ and $R_{31}$ are independently hydrogen, alkyl, alkenyl, alkynyl, monocyclic aryl or monocyclic heteroaryl.

26. The taxane of claim 25 wherein $R_2$ is —OCOR$_{31}$ and $R_{31}$ is as defined in claim 25.

27. The taxane of claim 25 wherein $R_{4a}$ is —OCOR$_{30}$ and $R_{30}$ is as defined in claim 25.

28. The taxane of claim 25 wherein $R_{7a}$ is hydroxy or protected hydroxy.

29. The taxane of claim 25 wherein $R_{10a}$ is —OCOR$_{29}$, and $R_{29}$ is as defined in claim 25.

30. The taxane of claim 25 wherein $R_2$ is —OCOR$_{31}$; $R_{4a}$ is —OCOR$_{30}$; $R_{10a}$ is —OCOR$_{29}$; $R_{14}$ is hydrogen; $R_{29}$ and $R_{30}$ are alkyl; and $R_{31}$ is aryl.

31. The taxane of claim 25 wherein $R_{4a}$ and $R_{10a}$ are acetoxy, and $R_2$ is benzoyloxy.

\* \* \* \* \*

UNITED STATES PATENT AND TRADEMARK OFFICE
CERTIFICATE OF CORRECTION

PATENT NO : 6,066,747
DATED : May 23, 2000
INVENTOR(S): Robert A. Holton, et al.

It is certified that error appears in the above-identified patent and that said Letters Patent are hereby corrected as shown below:

On the title page of the issued patent, add Related U.S. Application Data (section 62) to read --Continuation-in-part of Application No. 08/026,978, filed March 5, 1993, now U.S. Patent No. 5,990,325, and a continuation-in-part of Application No. 08/095,087, filed July 20, 1993, now abandoned.--.

Column 1, line 8, following "1994" insert--, which is a continuation-in-part of Application No. 08/026,978, filed March 5, 1993, now U.S. Patent No. 5,990,325, and a continuation-in-part of Application No. 08/095, 087, filed July 20, 1993, now abandoned.--.

Signed and Sealed this

Third Day of April, 2001

*Attest:*

NICHOLAS P. GODICI

*Attesting Officer*     *Acting Director of the United States Patent and Trademark Office*

UNITED STATES PATENT AND TRADEMARK OFFICE
CERTIFICATE OF CORRECTION

PATENT NO. : 6,066,747  
DATED : May 23, 2000  
INVENTOR(S) : Robert A. Holton et al.

Page 1 of 1

It is certified that error appears in the above-identified patent and that said Letters Patent is hereby corrected as shown below:

Column 1,
Lines 28-36, the chemical structures should read:

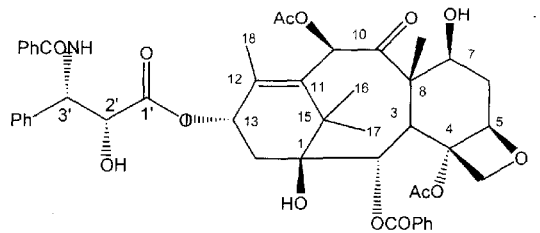

Column 38,
Lines 3-13, the chemical structure should read:

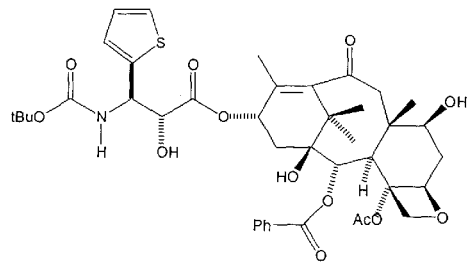

Signed and Sealed this

Seventeenth Day of August, 2004

JON W. DUDAS
*Acting Director of the United States Patent and Trademark Office*